United States Patent [19]
Tarczynski et al.

[11] Patent Number: 5,563,324
[45] Date of Patent: Oct. 8, 1996

[54] TRANSGENIC PLANTS WITH ALTERED POLYOL CONTENT

[75] Inventors: Mitchell C. Tarczynski; Richard G. Jensen; Hans J. Bohnert; Daniel M. Vernon, all of Tucson, Ariz.

[73] Assignee: The Arizona Board of Regents on behalf of the University of Arizona, Tucson, Ariz.

[21] Appl. No.: 186,833

[22] Filed: Jan. 25, 1994

Related U.S. Application Data

[63] Continuation of Ser. No. 871,416, Apr. 20, 1992, abandoned, which is a continuation-in-part of Ser. No. 697,390, May 9, 1991, abandoned.

[51] Int. Cl.$^6$ ............................... A01H 5/00; A01H 1/00; C12P 21/02; C12P 19/02

[52] U.S. Cl. .................. 800/205; 800/250; 800/DIG. 43; 435/172.3; 435/69.1; 435/70.1; 435/72; 435/190; 435/193; 47/58

[58] Field of Search .................................. 435/69.1, 70.1, 435/172.3, 72, 190, 193; 800/205, DIG. 43, 250; 47/58

[56] References Cited

U.S. PATENT DOCUMENTS 4,771,002  9/1988  Gelvin .................................. 435/172.3

OTHER PUBLICATIONS

F. Koller et al. Hoppe–Seyler's Z. Physiol. Chem., vol. 357 (Nov. 1976) pp. 1465–1468.
A. Fersht, Enzyme Structure & Mechanism, Reading & San Francisco, W. H. Freeman & Co., pp. 256–257 (1977).
P. Dittrich et al., Phytochemistry, vol. 26, #7 (1987) pp. 1925–1926.
R. Aebersold et al. PNAS, vol. 84 (Oct. 1987) pp. 6970–6974.
Sambrook, J., et al., "Molecular Cloning, A Laboratory Manual", Cold Spring Harbor Lab Press, Cold Spring Harbor, NY (1989), pp. 11.2–11.9, 11.45–11.49 , & 11.52–11.61.
An, G., et al., "Transformation of Tobacco, Tomato, Potato, and *Arabidopsis thaliana* Using a Binary Ti Vector System, " 81 *Plant Physiol.* 301–305 (1986).
Benfey, P. N. and Chua, N. H., "The Cauliflower Mosaic Virus 35S Promoter: Combinatorial Regulation of Transcription in Plants," 250 Science 959–966 (1990).
Bevan, M., "Binary *Agrobacterium* Vectors for Plant Transformation," 12 *Nucleic Acid Res.* 8710–8721 (1984).
Bieleski, R. L., "Sugar Alcohols," in 13A *Encycl. Plant Physiol.*, 158–192 (1986).
Davis, T., et al., "Nucleotide Sequence of the Mannitol (*mtl*) Operon in *Escherichia coli*," 2 Molecul. Microbiol. 405–412 (1988). Gives an incorrect sequence for *mtl* gene.
Fellman and W. H. Loescher, "Comparative Studies of Sucrose and Mannitol Utilization in Celery" (*Apium graveolens*) (1987).
Fox, T. C., et al., "Developmental Changes in Photosynthetic Gas Exchange in the Polyol–Synthesizing Species, *Apium graveolens* L., (Celery)," 82 *Plant Physiol.* 307–31 (1986).
Fromm, M., et al., "Expression of Genes Transferred into Monocot and Dicot Plant Cells by Electroporation," 82 PNAS 5824–5828 (1985).
Fromm, M. E., et al., "Stable Transformation of Maize After Gene Transfer by Electroporation," 319 *Nature* 791–793 (1986).
Guerineau, F., et al., "An Expression Cassette for Targeting Foreign Proteins into Chloroplasts," 16 N.A.R. 11380 (1980).
Harkins, K. R., et al., "Expression of Photosynthesis–Related Gene Fusions is Restricted by Cell Type in Transgenic Plants and Transfected Protoplasts," 87 *PNAS* 816–820 (1990).
Horsch, R. B., et al., "A Simple and General Method for Transferring Genes into Plants," 227 *Science* 1229–1231 (1985).
Ikawa, T., et al., "Enzymes Involved in the Last Steps of the Biosynthesis of Mannitol in Brown Algae," 13 *Plant Cell Physiol.* 1017–1029 (1972).
Jefferson, R. A., et al., "GUS Fusions: β–Glucuronidase as a Sensitive and Versatile Gene Fusion Marker in Higer Plants," 6 *EMBO J.* 3901–3911 (1987).
Jennings, D. H., "Polyol Metabolism in Fungi," 25 *Adv. Microbial. Physiol.* 149–193 (1984).
Jiang, W. and W. G. Niehaus, "Cloning and Sequencing of mtl D Gene from *Aspergillus parasiticus*," 107 J.C.B. 746A (1988) (abstract).
Jiang, W., et al., "The Corrected Sequence of the Mannitol (*mtl*) Operon in *Escherichia coli*," 4 *Molecul. Microbiol.* 2003–2006 (1990).
Lam, E. and Chua, N–H, "GT–1 Binding Site Confers Light Responsive Expression in Transgenic Tobacco," 248 *Science* 471–474 (1990).
Lee, C. A. and M. H. Saier, Jr., "Use of Cloned *mtl* Genes of *Escherichia coli* to Introduce *mtl* Deletion Mutations into the Chromosome," 153 *J. Bacteriology* 685–692 (1983).
Lee, Y. C., "High–Performance Anion—Exchange Chromatography for Carbohydrate Analysis," 189 *Anal. Biochem.* 152–162 (1990).

(List continued on next page.)

*Primary Examiner*—David T. Fox
*Assistant Examiner*—Charles Rories
*Attorney, Agent, or Firm*—Quarles & Brady

[57] ABSTRACT

Transgenic plants have been produced which have been engineered to produce physiologically significant levels of sugar alcohols, or polyols, which is not natively produced by plants of the species. Transgenic plants have been engineered to express a bacterial mannitol-1-P dehydrogenase which, in the reverse reaction in the plant cells, produces mannitol from fructose in a plant which does not natively produce mannitol. Levels of polyols in plant cells have been associated with osmotic regulation and thereby with water stress tolerance. The transgenic plants have significant research value, and, surprisingly, seem to exhibit enhanced growth rates and vigor, and stress tolerance. Another polyol-producing enzyme gene has been isolated from a stress tolerant plant.

23 Claims, 5 Drawing Sheets

OTHER PUBLICATIONS

Lewis, D. H., "Physiology and Metabolism of Alditols," In: Storage Carbohydrates in Vascular Plants, Ed by D. H. Lewis, *Cambridge University Press*, Cambridge, pp. 151–179 (1984).

Loescher, W. H., et al., "Other Carbohydrates as Translocated Carbon Sources: Acyclic Polyols and Photosynthetic Carbon Metabolism," In: Regulation of Carbon Partitioning in Photosynthetic Tissue. Ed by Heath, R. L. *Priess J. Am. Soc. Plant Physiol.*, Rockville, MD pp. 309–332 (1985).

Meinzer, F. C., et al., "Leaf Water Relations and Maintenance of Gas Exchange in Coffee Cultivars Grown in Drying Soil," 94 *Plant Physiol.* 1781–1787 (1990).

Napoli, C., et al., "Introduction of a Chimeric Chalcone Synthase Gene into Petunia Results in Reversible Co-Suppression of Homologous Genes *in trans,*" 2 *Plant Cell* 279–289 (1990).

Paul, M. J. and Cockburn, W., "Pinitol, a Compatible Solute in *Mesembryanthemum Crystallinum* L.?," 40 *J. Exper. Bot.* 1093–1098 (1989).

Peacock, J., et al., "Development and Environmental Regulation of the Maize Alcohol Dehydrogenase 1 (Adh1) Gene: Promoter–Enhancer Interactions" In: *Plant Gene Systems and Their Biology*, Ed Key J., McIntosh, L. AR Liss, New York, pp. 263–277 (1987).

Popp, M., "Chemical Composition of Australian Mangroves. II. Low Molecular Weight Carbohydrates," 113 *Z. Pflanzenphysiol.* 411–421 (1984).

Powlsen, C. and Chua N–H, "Dissection of 5' Upstream Sequences for Selective Expression of the *Nicotiana plumbaginifolia* rbcS–8B Gene." 214 *Mol. Gen. Genet.* 16–23 (1988).

Rocklin, R. D. and Pohl, C. A., "Determination of Carbohydrates by Anion Exchange Chromatography with Pulsed Amperometric Detection," 6 *J. Lig. Chromat.* 1577–1590 (1983).

Rumpho, M. E., et al., "A Pathway for Photosynthetic Carbon Flow to Mannitol in Celery Leaves," 73 *Plant Physiol.* 869–873 (1983).

Sharkey, T. D., "Photosynthesis in Intact Leaves of $C_3$ Plants: Physics, Physiology and Rate Limitations," 51 *Bot. Rev.* 53–105 (1985).

Thompson, M. R., et al., "Mannitol Metabolism in Cultured Plant Cells," 67 *Physiol. Plant* 365–369 (1986).

Trip, P., et al., "Metabolism of Mannitol in Higher Plants," 51 *Am. J. Bot.* 828–835 (1964).

Tyree, M. T., "The Relationship Between the Bulk Modules of Elasticity of a Complex Tissue and the Mean Modules of its Cells." *Ann. Bot.* 47:547–559 (1981).

van der Krol, A. R., et al., "Flavonoid Genes in Petunia: Addition of a Limited Number of Genes Copies May Lead to a Suppression of Gene Expression," 2 *Plant Cell* 291–299 (1990).

von Schaewen, A., et al., "Expression of a Yeast–Derived Invertase in the Cell Wall of Tobacco and Arabidopsis Plants Leads to Accumulation of Carbohydrate and Inhibition of Photosynthesis and Strongly Influences Growth and Phenotype of Transgenic Tobacco Plants," 9 EMBO Journal 3033–3044 (1990).

Wyn Jones, R. G., et al., "A Hypothesis on Cytoplasmic Osmoregulation" In: Regulation of Cell Membrane Activities in Plants. Ed. Marre E. Elsevier/North Holland Biomed Press, Amsterdam. pp. 121–136 (1997).

Lewis, D. H. and D. C. Smith, "Sugar Alcohols (Polyols) in Fungi and Green Plants, I. Distribution, Physiology and Metabolism," 66 *New Phytol.* 143–184 (1967).

Cushman, J. C., et al., "Salt Stress Leads to Differential Expression of Two Isogenes of Phosphoenolpyruvate Carboxylase during Crassulacean Acid Metabolism Induction in the Common Ice Pland", 1 *Plant Cell* 715–725 (1989).

Sivak, M. N., "Increasing Photosynthesis by Genetic Manipulation: Difficulties and Prospects," In: Enzymatic and Model Carboxylation and Reduction Reactions for Carbon Dioxide Utilization, Ed. by M. Aresta and J. V. Schloss, Kluwer Academic Publishers, Netherlands. pp. 301–320 (1990).

Tarczynski, et al., "Expression of a Bacterial *mtlD* gene in Transgeric Tobacco Leads to Production and Accumulation of Mannitol," 89 *Proc. Natl. Acad. Sci.* (1992) (print draft).

Vernon D. M. and H. J. Bohnert, "A Novel Methyl Transferase Inducted by Osmotic Stress in the Faculative Halophyte *Mesembryanthemum crystalliunm,*" EMBO (Manuscript).

Tarczynski, et al., "Stress Protection of Transgenic Tobacco by Production of the Osmolyte Mannitol," *Science*, vol. 259, 508–510 (1993).

Vernon et al., "Cyclitol production in transgenic tobacco," *The Plant Journal* 4(1), 199–205 (1993).

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 1153 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Escherichia coli
        ( B ) STRAIN: mtlD mutant 239

( i x ) FEATURE:
        ( A ) NAME/KEY: CDS
        ( B ) LOCATION: 5..1153
        ( C ) IDENTIFICATION METHOD: experimental
        ( D ) OTHER INFORMATION: /codon_start=5
                / product="mannitol-1 dehydrogenase"
                / evidence=EXPERIMENTAL
                / gene="mtlD"
                / number=1

( x i ) SEQUENCE DESCRIPTION: SEQ ID NO:1:

```
ACTT ATG  AAA  GCA  TTA  CAT  TTT  GGC  GCA  GGT  AAT  ATC  GGT  CGT  GGC  TTT       49
     Met  Lys  Ala  Leu  His  Phe  Gly  Ala  Gly  Asn  Ile  Gly  Arg  Gly  Phe
     1              5                        10                       15

ATC  GGT  AAA  CTG  CTG  GCA  GAC  GCG  GGT  ATC  CAA  CTG  ACG  TTT  GCC  GAT       97
Ile  Gly  Lys  Leu  Leu  Ala  Asp  Ala  Gly  Ile  Gln  Leu  Thr  Phe  Ala  Asp
                    20                       25                       30

GTC  AAT  CAG  GTG  GTA  CTT  GAT  GCC  CTG  AAT  GCC  CGT  CAT  AGC  TAT  CAG      145
Val  Asn  Gln  Val  Val  Leu  Asp  Ala  Leu  Asn  Ala  Arg  His  Ser  Tyr  Gln
               35                       40                       45

GTA  CAT  GTG  GTT  GGT  GAA  ACC  GAG  CAG  GTA  GAT  ACC  GTT  TCC  GGC  GTC      193
Val  His  Val  Val  Gly  Glu  Thr  Glu  Gln  Val  Asp  Thr  Val  Ser  Gly  Val
          50                       55                       60

AAT  GCT  GTC  AGC  AGC  ATT  GGT  GAT  GAT  GTC  GTT  GAT  CTG  ATT  GCT  CAG      241
Asn  Ala  Val  Ser  Ser  Ile  Gly  Asp  Asp  Val  Val  Asp  Leu  Ile  Ala  Gln
     65                       70                       75

GTT  GAT  TTA  GTC  ACT  ACC  CGC  GTT  GGC  CCG  GTT  GTG  CTG  GAA  CGT  ATT      289
Val  Asp  Leu  Val  Thr  Thr  Arg  Val  Gly  Pro  Val  Val  Leu  Glu  Arg  Ile
80                       85                       90                       95

GCA  CCG  GCA  ATC  GCC  AAA  GGG  CAG  GTG  AAA  CGT  AAA  GAA  CAA  GGT  AAT      337
Ala  Pro  Ala  Ile  Ala  Lys  Gly  Gln  Val  Lys  Arg  Lys  Glu  Gln  Gly  Asn
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     |     | 100 |     |     |     |     |     | 105 |     |     |     |     | 110 |      |
| GAA | TCC | CCG | CTG | AAC | ATC | ATC | GCC | TGT | GAA | AAC | ATG | GTA | CGC | GGT | ACC | 385  |
| Glu | Ser | Pro | Leu | Asn | Ile | Ile | Ala | Cys | Glu | Asn | Met | Val | Arg | Gly | Thr |      |
|     |     |     | 115 |     |     |     |     | 120 |     |     |     |     | 125 |     |     |      |
| ACG | CAG | CTG | AAA | GGC | CAT | GTG | ATG | AAC | GCC | CTG | CCG | GAA | GAC | GCC | AAA | 433  |
| Thr | Gln | Leu | Lys | Gly | His | Val | Met | Asn | Ala | Leu | Pro | Glu | Asp | Ala | Lys |      |
|     |     | 130 |     |     |     |     | 135 |     |     |     |     | 140 |     |     |     |      |
| GCG | TGG | GTA | GAA | GAA | CAC | GTT | GGC | TTT | GTC | GAT | TCC | GCC | GTT | GAC | CGC | 481  |
| Ala | Trp | Val | Glu | Glu | His | Val | Gly | Phe | Val | Asp | Ser | Ala | Val | Asp | Arg |      |
|     | 145 |     |     |     |     | 150 |     |     |     |     | 155 |     |     |     |     |      |
| ATC | GTA | CCG | CCT | TCG | GCT | TCG | GCA | ACT | AAC | GAT | CCG | CTG | GAA | GTG | ACG | 529  |
| Ile | Val | Pro | Pro | Ser | Ala | Ser | Ala | Thr | Asn | Asp | Pro | Leu | Glu | Val | Thr |      |
| 160 |     |     |     |     | 165 |     |     |     |     | 170 |     |     |     |     | 175 |      |
| GTA | GAA | ACC | TTC | AGC | GAA | TGG | ATT | GTC | GAT | AAA | ACG | CAG | TTC | AAA | GGC | 577  |
| Val | Glu | Thr | Phe | Ser | Glu | Trp | Ile | Val | Asp | Lys | Thr | Gln | Phe | Lys | Gly |      |
|     |     |     |     | 180 |     |     |     |     | 185 |     |     |     |     | 190 |     |      |
| GCA | CTG | CCG | AAC | ATC | CCA | GGC | ATG | GAG | TTA | ACC | GAC | AAC | CTG | ATG | GCA | 625  |
| Ala | Leu | Pro | Asn | Ile | Pro | Gly | Met | Glu | Leu | Thr | Asp | Asn | Leu | Met | Ala |      |
|     |     |     | 195 |     |     |     |     | 200 |     |     |     |     | 205 |     |     |      |
| TTT | GTC | GAA | CGT | AAA | CTC | TTC | ACC | CTG | AAC | ACG | GGT | CAT | GCT | ATA | ACC | 673  |
| Phe | Val | Glu | Arg | Lys | Leu | Phe | Thr | Leu | Asn | Thr | Gly | His | Ala | Ile | Thr |      |
|     |     | 210 |     |     |     |     | 215 |     |     |     |     | 220 |     |     |     |      |
| GCG | TAC | CTC | GGA | AAA | CTG | GCC | GGT | CAT | CAG | ACC | ATT | CGT | GAC | GCG | ATT | 721  |
| Ala | Tyr | Leu | Gly | Lys | Leu | Ala | Gly | His | Gln | Thr | Ile | Arg | Asp | Ala | Ile |      |
|     | 225 |     |     |     |     | 230 |     |     |     |     | 235 |     |     |     |     |      |
| CTC | GAC | GAG | AAA | ATC | CGC | GCG | GTG | GTA | AAA | GGT | GCG | ATG | GAA | GAA | AGT | 769  |
| Leu | Asp | Glu | Lys | Ile | Arg | Ala | Val | Val | Lys | Gly | Ala | Met | Glu | Glu | Ser |      |
| 240 |     |     |     |     | 245 |     |     |     |     | 250 |     |     |     |     | 255 |      |
| GGT | GCA | GTA | TTG | ATC | AAG | CGC | TAC | GGC | TTT | GAC | GCT | GAC | AAG | CAT | GCG | 817  |
| Gly | Ala | Val | Leu | Ile | Lys | Arg | Tyr | Gly | Phe | Asp | Ala | Asp | Lys | His | Ala |      |
|     |     |     |     | 260 |     |     |     |     | 265 |     |     |     |     | 270 |     |      |
| GCG | TAC | ATC | CAG | AAA | ATT | CTC | GGC | CGT | TTT | GAG | AAC | CCG | TAT | CTG | AAA | 865  |
| Ala | Tyr | Ile | Gln | Lys | Ile | Leu | Gly | Arg | Phe | Glu | Asn | Pro | Tyr | Leu | Lys |      |
|     |     |     | 275 |     |     |     |     | 280 |     |     |     |     | 285 |     |     |      |
| GAT | GAT | GTA | GAG | CGC | GTA | GGC | CGT | CAG | CCA | CTG | CGT | AAA | CTG | AGT | GCT | 913  |
| Asp | Asp | Val | Glu | Arg | Val | Gly | Arg | Gln | Pro | Leu | Arg | Lys | Leu | Ser | Ala |      |
|     |     | 290 |     |     |     |     | 295 |     |     |     |     | 300 |     |     |     |      |
| GGC | GAC | CGT | CTG | ATC | AAG | CCA | CTG | CTC | GGT | ACG | CTG | GAA | TAT | GGT | CTG | 961  |
| Gly | Asp | Arg | Leu | Ile | Lys | Pro | Leu | Leu | Gly | Thr | Leu | Glu | Tyr | Gly | Leu |      |
|     | 305 |     |     |     |     | 310 |     |     |     |     | 315 |     |     |     |     |      |
| CCA | CAT | AAA | AAC | CTG | ATT | GAA | GGT | ATT | GCC | GCT | GCA | ATG | CAC | TTC | CGC | 1009 |
| Pro | His | Lys | Asn | Leu | Ile | Glu | Gly | Ile | Ala | Ala | Ala | Met | His | Phe | Arg |      |
| 320 |     |     |     |     | 325 |     |     |     |     | 330 |     |     |     |     | 335 |      |
| AGT | GAA | GAT | GAT | CCG | CAG | GCT | CAG | GAA | CTG | GCA | GCA | CTG | ATC | GCT | GAC | 1057 |
| Ser | Glu | Asp | Asp | Pro | Gln | Ala | Gln | Glu | Leu | Ala | Ala | Leu | Ile | Ala | Asp |      |
|     |     |     |     | 340 |     |     |     |     | 345 |     |     |     |     | 350 |     |      |
| AAA | GGT | CCG | CAG | GCG | GCG | CTG | GCA | CAG | ATT | TCC | GGT | CTT | GAT | GCC | AAC | 1105 |
| Lys | Gly | Pro | Gln | Ala | Ala | Leu | Ala | Gln | Ile | Ser | Gly | Leu | Asp | Ala | Asn |      |
|     |     |     | 355 |     |     |     |     | 360 |     |     |     |     | 365 |     |     |      |
| AGC | GAG | GTT | GTA | TCC | GAG | GCG | GTA | ACC | GCT | TAT | AAA | GCA | ATG | CAA | TAA | 1153 |
| Ser | Glu | Val | Val | Ser | Glu | Ala | Val | Thr | Ala | Tyr | Lys | Ala | Met | Gln |     |      |
|     |     | 370 |     |     |     | 375 |     |     |     |     | 380 |     |     |     |     |      |

( 2 ) INFORMATION FOR SEQ ID NO:2:

( i ) SEQUENCE CHARACTERISTICS:
        ( A ) LENGTH: 382 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met<br>1 | Lys | Ala | Leu | His<br>5 | Phe | Gly | Ala | Gly | Asn<br>10 | Ile | Gly | Arg | Gly | Phe<br>15 | Ile |
| Gly | Lys | Leu | Leu<br>20 | Ala | Asp | Ala | Gly | Ile<br>25 | Gln | Leu | Thr | Phe | Ala<br>30 | Asp | Val |
| Asn | Gln | Val<br>35 | Val | Leu | Asp | Ala | Leu<br>40 | Asn | Ala | Arg | His | Ser<br>45 | Tyr | Gln | Val |
| His | Val<br>50 | Val | Gly | Glu | Thr | Glu<br>55 | Gln | Val | Asp | Thr | Val<br>60 | Ser | Gly | Val | Asn |
| Ala<br>65 | Val | Ser | Ser | Ile | Gly<br>70 | Asp | Asp | Val | Val | Asp<br>75 | Leu | Ile | Ala | Gln | Val<br>80 |
| Asp | Leu | Val | Thr | Thr<br>85 | Arg | Val | Gly | Pro | Val<br>90 | Val | Leu | Glu | Arg | Ile<br>95 | Ala |
| Pro | Ala | Ile | Ala<br>100 | Lys | Gly | Gln | Val | Lys<br>105 | Arg | Lys | Glu | Gln | Gly<br>110 | Asn | Glu |
| Ser | Pro | Leu<br>115 | Asn | Ile | Ile | Ala | Cys<br>120 | Glu | Asn | Met | Val | Arg<br>125 | Gly | Thr | Thr |
| Gln | Leu<br>130 | Lys | Gly | His | Val | Met<br>135 | Asn | Ala | Leu | Pro | Glu<br>140 | Asp | Ala | Lys | Ala |
| Trp<br>145 | Val | Glu | Glu | His | Val<br>150 | Gly | Phe | Val | Asp | Ser<br>155 | Ala | Val | Asp | Arg | Ile<br>160 |
| Val | Pro | Pro | Ser | Ala<br>165 | Ser | Ala | Thr | Asn | Asp<br>170 | Pro | Leu | Glu | Val | Thr<br>175 | Val |
| Glu | Thr | Phe | Ser<br>180 | Glu | Trp | Ile | Val | Asp<br>185 | Lys | Thr | Gln | Phe | Lys<br>190 | Gly | Ala |
| Leu | Pro | Asn<br>195 | Ile | Pro | Gly | Met | Glu<br>200 | Leu | Thr | Asp | Asn | Leu<br>205 | Met | Ala | Phe |
| Val | Glu<br>210 | Arg | Lys | Leu | Phe | Thr<br>215 | Leu | Asn | Thr | Gly | His<br>220 | Ala | Ile | Thr | Ala |
| Tyr<br>225 | Leu | Gly | Lys | Leu | Ala<br>230 | Gly | His | Gln | Thr | Ile<br>235 | Arg | Asp | Ala | Ile | Leu<br>240 |
| Asp | Glu | Lys | Ile | Arg<br>245 | Ala | Val | Val | Lys | Gly<br>250 | Ala | Met | Glu | Glu | Ser<br>255 | Gly |
| Ala | Val | Leu | Ile<br>260 | Lys | Arg | Tyr | Gly | Phe<br>265 | Asp | Ala | Asp | Lys | His<br>270 | Ala | Ala |
| Tyr | Ile | Gln<br>275 | Lys | Ile | Leu | Gly | Arg<br>280 | Phe | Glu | Asn | Pro | Tyr<br>285 | Leu | Lys | Asp |
| Asp | Val<br>290 | Glu | Arg | Val | Gly | Arg<br>295 | Gln | Pro | Leu | Arg | Lys<br>300 | Leu | Ser | Ala | Gly |
| Asp<br>305 | Arg | Leu | Ile | Lys | Pro<br>310 | Leu | Leu | Gly | Thr | Leu<br>315 | Glu | Tyr | Gly | Leu | Pro<br>320 |
| His | Lys | Asn | Leu | Ile<br>325 | Glu | Gly | Ile | Ala | Ala<br>330 | Ala | Met | His | Phe | Arg<br>335 | Ser |
| Glu | Asp | Asp | Pro<br>340 | Gln | Ala | Gln | Glu | Leu<br>345 | Ala | Ala | Leu | Ile | Ala<br>350 | Asp | Lys |
| Gly | Pro | Gln | Ala<br>355 | Ala | Leu | Ala | Gln | Ile<br>360 | Ser | Gly | Leu | Asp<br>365 | Ala | Asn | Ser |
| Glu | Val<br>370 | Val | Ser | Glu | Ala | Val<br>375 | Thr | Ala | Tyr | Lys | Ala<br>380 | Met | Gln | | |

( 2 ) INFORMATION FOR SEQ ID NO:3:

( i ) SEQUENCE CHARACTERISTICS:
( A ) LENGTH: 1525 base pairs
( B ) TYPE: nucleic acid ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( A ) ORGANISM: Mesembryanthemum crystallinum ( v i i ) IMMEDIATE SOURCE:
        ( B ) CLONE: Imt1

( i x ) FEATURE:
        ( A ) NAME/KEY: CDS
        ( B ) LOCATION: 47..1141

( x i ) SEQUENCE DESCRIPTION: SEQ ID NO:3:

```
AAAAAAAAAA TTTTACTTCT CTGTTTTACC AAAAAGAGAA AAAAAA ATG ACT ACT           55
                                                    Met Thr Thr
                                                     1

TAC ACC AAT GGC AAC TAC ACA CAA CCA AAA ACC CTA GAC AAA GAT GAA         103
Tyr Thr Asn Gly Asn Tyr Thr Gln Pro Lys Thr Leu Asp Lys Asp Glu
     5              10                  15

CAA TTA GCT GGT TTG GCA GTG ACA TTA GCA AAT GCA GCT GCT TTT CCA         151
Gln Leu Ala Gly Leu Ala Val Thr Leu Ala Asn Ala Ala Ala Phe Pro
 20              25                  30                  35

ATG ATC CTG AAA TCA GCC TTT GAG CTA AAA ATC CTT GAC ATA TTC TCA         199
Met Ile Leu Lys Ser Ala Phe Glu Leu Lys Ile Leu Asp Ile Phe Ser
                 40                  45                  50

AAA GCA GGG GAA GGC GTG TTT GTA TCG ACT TCT GAG ATC GCT AGC CAA         247
Lys Ala Gly Glu Gly Val Phe Val Ser Thr Ser Glu Ile Ala Ser Gln
             55                  60                  65

ATC GGG GCA AAG AAC CCT AAT GCC CCG GTG TTG TTG GAC CGG ATG CTC         295
Ile Gly Ala Lys Asn Pro Asn Ala Pro Val Leu Leu Asp Arg Met Leu
         70                  75                  80

CGG CTC CTG GCT AGC CAC TCT GTG TTA ACA TGC AAG CTC CAA AAG GGT         343
Arg Leu Leu Ala Ser His Ser Val Leu Thr Cys Lys Leu Gln Lys Gly
     85                  90                  95

GAG GGT GGT TCT CAA AGG GTG TAT GGT CCA GCT CCC CTT TGC AAC TAT         391
Glu Gly Gly Ser Gln Arg Val Tyr Gly Pro Ala Pro Leu Cys Asn Tyr
100                 105                 110                 115

CTT GCT AGT AAT GAT GGT CAA GGC TCT CTT GGC CCT TTG CTT GTT TTG         439
Leu Ala Ser Asn Asp Gly Gln Gly Ser Leu Gly Pro Leu Leu Val Leu
                120                 125                 130

CAT CAT GAC AAG GTC ATG ATG GAG AGT TGG TTT CAC TTG AAT GAT TAC         487
His His Asp Lys Val Met Met Glu Ser Trp Phe His Leu Asn Asp Tyr
            135                 140                 145

ATA CTA GAA GGA GGT GTT CCA TTC AAG CGC GCT CAT GGG ATG ATC CAA         535
Ile Leu Glu Gly Gly Val Pro Phe Lys Arg Ala His Gly Met Ile Gln
        150                 155                 160

TTC GAC TAC ACT GGG ACT GAT GAA AGG TTC AAT CAT GTG TTC AAC CAA         583
Phe Asp Tyr Thr Gly Thr Asp Glu Arg Phe Asn His Val Phe Asn Gln
    165                 170                 175

GGG ATG GCA CAC CAC ACT ATC CTG GTC ATG AAG AAG CTC CTT GAC AAC         631
Gly Met Ala His His Thr Ile Leu Val Met Lys Lys Leu Leu Asp Asn
180                 185                 190                 195

TAC AAT GGG TTT AAT GAT GTC AAG GTC CTA GTT GAT GTG GGT GGT AAC         679
Tyr Asn Gly Phe Asn Asp Val Lys Val Leu Val Asp Val Gly Gly Asn
                200                 205                 210

ATT GGT GTC AAT GTG AGC ATG ATC GTC GCT AAG CAT ACT CAC ATT AAG         727
Ile Gly Val Asn Val Ser Met Ile Val Ala Lys His Thr His Ile Lys
            215                 220                 225
```

| | | | | | | | | | | | | | | | | |
|---|---|---|---|---|---|---|---|---|---|---|---|---|---|---|---|---|
| GGC | ATC | AAC | TAT | GAC | TTG | CCT | CAT | GTC | ATT | GCT | GAT | GCT | CCT | TCT | TAC | 775 |
| Gly | Ile | Asn | Tyr | Asp | Leu | Pro | His | Val | Ile | Ala | Asp | Ala | Pro | Ser | Tyr | |
| | | 230 | | | | 235 | | | | | 240 | | | | | |
| CCC | GGT | GTG | GAG | CAT | GTT | GGT | GGT | AAC | ATG | TTT | GAG | AGC | ATA | CCA | CAA | 823 |
| Pro | Gly | Val | Glu | His | Val | Gly | Gly | Asn | Met | Phe | Glu | Ser | Ile | Pro | Gln | |
| | 245 | | | | | 250 | | | | | 255 | | | | | |
| GCA | GAT | GCC | ATT | TTC | ATG | AAG | TGG | GTG | TTG | CAT | GAT | TGG | AGC | GAC | GAG | 871 |
| Ala | Asp | Ala | Ile | Phe | Met | Lys | Trp | Val | Leu | His | Asp | Trp | Ser | Asp | Glu | |
| 260 | | | | | 265 | | | | | 270 | | | | | 275 | |
| CAT | TGC | GTG | AAG | ATA | CTC | AAC | AAG | TGC | TAT | GAG | AGC | CTG | GCA | AAG | GGA | 919 |
| His | Cys | Val | Lys | Ile | Leu | Asn | Lys | Cys | Tyr | Glu | Ser | Leu | Ala | Lys | Gly | |
| | | | | 280 | | | | | 285 | | | | | 290 | | |
| GGG | AAG | ATC | ATC | CTT | GTG | GAA | TCG | CTT | ATA | CCA | GTA | ATC | CCA | GAA | GAC | 967 |
| Gly | Lys | Ile | Ile | Leu | Val | Glu | Ser | Leu | Ile | Pro | Val | Ile | Pro | Glu | Asp | |
| | | | 295 | | | | | 300 | | | | | 305 | | | |
| AAC | CTC | GAA | TCA | CAC | ATG | GTG | TTT | AGC | CTT | GAT | TGC | CAC | ACT | TTG | GTG | 1015 |
| Asn | Leu | Glu | Ser | His | Met | Val | Phe | Ser | Leu | Asp | Cys | His | Thr | Leu | Val | |
| | | 310 | | | | | 315 | | | | | 320 | | | | |
| CAC | AAC | CAA | GGT | GGA | AAA | GAG | AGA | TCA | AAG | GAG | GAT | TTT | GAA | GCC | TTA | 1063 |
| His | Asn | Gln | Gly | Gly | Lys | Glu | Arg | Ser | Lys | Glu | Asp | Phe | Glu | Ala | Leu | |
| | 325 | | | | | 330 | | | | | 335 | | | | | |
| GCT | TCC | AAG | ACT | GGC | TTC | TCT | ACA | GTT | GAT | GTC | ATT | TGC | TGT | GCC | TAT | 1111 |
| Ala | Ser | Lys | Thr | Gly | Phe | Ser | Thr | Val | Asp | Val | Ile | Cys | Cys | Ala | Tyr | |
| 340 | | | | | 345 | | | | | 350 | | | | | 355 | |
| GAC | ACT | TGG | GTC | ATG | GAG | CTC | TAC | AAG | AAG | TGATTCAAGC | TCTAAATGCT | | | | | 1161 |
| Asp | Thr | Trp | Val | Met | Glu | Leu | Tyr | Lys | Lys | | | | | | | |
| | | | | 360 | | | | | 365 | | | | | | | |

| | | | | | |
|---|---|---|---|---|---|
| GTGTTGTTGT | CATTGTTGCT | AGCCCAAGTA | GCTAGCTAGC | TGGTTAAAAT | TTCTCCTACC | 1221 |
| TAGCATTTGT | TTTATGGCTA | AGTTGAGGAG | ATTCATGTAT | TGTAAATGTT | GTGTTTGGGT | 1281 |
| TTGGGTTTGT | ATTTGTATTT | GTGTTTTGTT | GTTGTGTCTT | TGTAGCTAAG | TTGATATCCT | 1341 |
| GCTCATCTAG | GCTGGCTGCA | TTTTTTTTGT | GGCTGCCTTA | CAATGTAGCA | TTTGTGGTTT | 1401 |
| TCTTTCAATA | AAGCATCTAT | TGTACCTCTG | TTATCAGTGT | ATGATTTGCC | TTTATTTTTA | 1461 |
| ATAACTTAAT | TTTTTTTTC | TTGTTTATAT | CCAAAAAAAA | AAAAAAAAAA | AAAAAAAAA | 1521 |
| AAAC | | | | | | 1525 |

(2) INFORMATION FOR SEQ ID NO:4:

(i) SEQUENCE CHARACTERISTICS:
        (A) LENGTH: 365 amino acids
        (B) TYPE: amino acid
        (D) TOPOLOGY: linear (ii) MOLECULE TYPE: protein (xi) SEQUENCE DESCRIPTION: SEQ ID NO:4:

| | | | | | | | | | | | | | | | |
|---|---|---|---|---|---|---|---|---|---|---|---|---|---|---|---|
| Met | Thr | Thr | Tyr | Thr | Asn | Gly | Asn | Tyr | Thr | Gln | Pro | Lys | Thr | Leu | Asp |
| 1 | | | | 5 | | | | | 10 | | | | | 15 | |
| Lys | Asp | Glu | Gln | Leu | Ala | Gly | Leu | Ala | Val | Thr | Leu | Ala | Asn | Ala | Ala |
| | | | 20 | | | | | 25 | | | | | 30 | | |
| Ala | Phe | Pro | Met | Ile | Leu | Lys | Ser | Ala | Phe | Glu | Leu | Lys | Ile | Leu | Asp |
| | | 35 | | | | | 40 | | | | | 45 | | | |
| Ile | Phe | Ser | Lys | Ala | Gly | Glu | Gly | Val | Phe | Val | Ser | Thr | Ser | Glu | Ile |
| | 50 | | | | | 55 | | | | | 60 | | | | |
| Ala | Ser | Gln | Ile | Gly | Ala | Lys | Asn | Pro | Asn | Ala | Pro | Val | Leu | Leu | Asp |
| 65 | | | | | 70 | | | | | 75 | | | | | 80 |
| Arg | Met | Leu | Arg | Leu | Leu | Ala | Ser | His | Ser | Val | Leu | Thr | Cys | Lys | Leu |
| | | | | 85 | | | | | 90 | | | | | 95 | |

| | | | | | | | | | | | | | | | |
|---|---|---|---|---|---|---|---|---|---|---|---|---|---|---|---|
| Gln | Lys | Gly | Glu 100 | Gly | Gly | Ser | Gln | Arg 105 | Val | Tyr | Gly | Pro | Ala 110 | Pro | Leu |
| Cys | Asn | Tyr 115 | Leu | Ala | Ser | Asn | Asp 120 | Gly | Gln | Gly | Ser | Leu 125 | Gly | Pro | Leu |
| Leu | Val 130 | Leu | His | His | Asp | Lys 135 | Val | Met | Met | Glu | Ser 140 | Trp | Phe | His | Leu |
| Asn 145 | Asp | Tyr | Ile | Leu | Glu 150 | Gly | Gly | Val | Pro | Phe 155 | Lys | Arg | Ala | His | Gly 160 |
| Met | Ile | Gln | Phe | Asp 165 | Tyr | Thr | Gly | Thr | Asp 170 | Glu | Arg | Phe | Asn | His 175 | Val |
| Phe | Asn | Gln | Gly 180 | Met | Ala | His | His | Thr 185 | Ile | Leu | Val | Met | Lys 190 | Lys | Leu |
| Leu | Asp | Asn 195 | Tyr | Asn | Gly | Phe | Asn 200 | Asp | Val | Lys | Val | Leu 205 | Val | Asp | Val |
| Gly | Gly 210 | Asn | Ile | Gly | Val | Asn 215 | Val | Ser | Met | Ile | Val 220 | Ala | Lys | His | Thr |
| His 225 | Ile | Lys | Gly | Ile | Asn 230 | Tyr | Asp | Leu | Pro | His 235 | Val | Ile | Ala | Asp | Ala 240 |
| Pro | Ser | Tyr | Pro | Gly 245 | Val | Glu | His | Val | Gly 250 | Gly | Asn | Met | Phe | Glu 255 | Ser |
| Ile | Pro | Gln | Ala 260 | Asp | Ala | Ile | Phe | Met 265 | Lys | Trp | Val | Leu | His 270 | Asp | Trp |
| Ser | Asp | Glu 275 | His | Cys | Val | Lys | Ile | Leu 280 | Asn | Lys | Cys | Tyr 285 | Glu | Ser | Leu |
| Ala | Lys 290 | Gly | Gly | Lys | Ile | Ile 295 | Leu | Val | Glu | Ser | Leu 300 | Ile | Pro | Val | Ile |
| Pro 305 | Glu | Asp | Asn | Leu | Glu 310 | Ser | His | Met | Val | Phe 315 | Ser | Leu | Asp | Cys | His 320 |
| Thr | Leu | Val | His | Asn 325 | Gln | Gly | Gly | Lys | Glu 330 | Arg | Ser | Lys | Glu | Asp 335 | Phe |
| Glu | Ala | Leu | Ala 340 | Ser | Lys | Thr | Gly | Phe 345 | Ser | Thr | Val | Asp | Val 350 | Ile | Cys |
| Cys | Ala | Tyr 355 | Asp | Thr | Trp | Val | Met 360 | Glu | Leu | Tyr | Lys | Lys 365 | | | |

TRANSGENIC PLANTS WITH ALTERED POLYOL CONTENT

CROSS REFERENCE TO RELATED APPLICATION

This is a continuation, of application Ser. No. 07/871,416, filed Apr. 20, 1992, now abandoned, which is a continuation-in-part of Ser. No. 07/697,390 filed May 9, 1991, now abandoned.

FIELD OF THE INVENTION

The present invention relates to the general field of the genetic engineering of higher plants and relates, in particular, to the creation of transgenic plants which have been engineered to produce elevated levels of polyhydroxylated sugars or polyols.

BACKGROUND OF THE INVENTION

One of the applications of modern biotechnology has been to enable the genetic engineering of higher plants. By the term genetic engineering, as used here, it is intended to describe the insertion into the inheritable genetic material of a plant one or more foreign, usually chimeric, genes which are either not natively present in the plant genome or are not present in the plant in that form. The transformed plant itself and its progeny which carry the inserted gene are referred to as transgenic plants, and the inserted gene may sometimes be referred to as a transgene. It is important that the inserted foreign gene be inheritable by progeny of the original engineered plant by normal sexual Mendelian inheritance, in other words that the germ line of the plant be transformed.

The first, and still most widely used, method of the genetic engineering of plants is based on the ability of a natural plant pathogen, *Agrobacterium tumefaciens*, to insert a portion of its plasmid DNA, referred to at its T-DNA (transfer DNA), into a host plant. The Agrobacterium plasmid which is responsible for this ability is known as "Ti" plasmid, for tumor-inducing, since the native function of the plasmid is to induce in infected plant cells an oncogenic process which also produces metabolites on which the bacteria feeds. Scientists have learned how to remove the oncogenic capability from, or "disarm," the Ti plasmid from Agrobacterium, and then to insert into the T-DNA of the disarmed Ti plasmid the foreign gene which is sought to be inserted into the plant. The Agrobacterium carrying the altered Ti plasmid is then allowed to infect susceptible plant cells, and its transfer process carries the foreign gene or genes in the T-DNA into the plant cells. If a selectable resistance marker, i.e. a transgene which confers resistance to an antibiotic or herbicide to which the plant is susceptible, is incorporated into the Ti plasmid, the selection agent can be used to select for the transformed plant cells. The transformed cells can then be regenerated into whole sexually mature plants.

The techniques of Agrobacterium-mediated plant transformation have been applied to a large number of plants including tobacco, tomato, petunia, cotton, carrot, soybean and walnut. The technique may be limited in some plants, however, due to limitations in the host range of Agrobacterium species (notably to dicot plants) and the lack of regeneration protocols for some plants. Other approaches have enabled the genetic engineering of most of the important plant species not susceptible to Agrobacterium transformation. It is possible to introduce genes into individual plant cells by electroporation, involving electric shock, or by chemical cell wall disruption using polyethylene glycol, and these techniques have been used to transform protoplasts of rice and other cereals, which are not Agrobacterium hosts. For species which can be regenerated from protoplasts, this approach is practical. Another recently developed technique makes use of microprojectiles coated with DNA, which are physically accelerated into plant cells. This acceleration particle transformation technique has been reported to work with tissue cultures of tobacco, with suspension cultures of maize and cotton, and with meristematic tissue of soybean, poplar, and cotton.

In general, while transgenic plants are, of course, somewhat different from native plants of the species, they are generally not radically altered. The transgenic plants may carry one or more, sometimes many, copies of an inserted foreign gene. The inserted genes can often be expressed, although for the genes that are expressed, the level of expression will vary depending on variables such as copy number, site of insertion (which is believed random), strength of promoter or enhancers, and character of coding sequence. Since copy number and insertion site vary with each transformation event, it is usually the case that several independently transgenic plant families or lines are created, which may have slightly different expression characteristics. In general, there do not appear to be fundamental differences among the transgenic plants created by any of these methods, i.e. there is variation in the plants, but it is independent of the method of transformation. In any event, while not all plants have yet been genetically engineered, the presently available techniques, and the wide variety of plants to which they have been applied, suggest that there are no biological barriers to the genetic engineering of any plant species.

In the study of transgenic plants, tobacco and Arapidopsis are often used as model systems. This is because tobacco is generally one of the easiest plants to genetically engineer by Agrobacterium transformation, due to the availability well-known and convenient selectable markers, and ready regeneration protocols. In general, transgenes which have been expressed well in tobacco have been demonstrated to express with similar characteristics in other plant species. Tobacco is also typical of stress sensitive crop plants in its osmotic regulation and sugar synthesis. Tobacco does not natively produce mannitol in its tissues and has been reported to be unable to metabolize mannitol.

While the procedures for the genetic engineering of most of the important agricultural crop species have now been developed, there has been somewhat less progress in the identification of what foreign traits or genes may be usefully inserted into plants. The best known examples so far in the technology involve genes which confer resistances, for example resistances to herbicides or to pests. Such genes can confer the desired trait (i.e. resistance) with a single transgene. To improve some of the more agronomically important traits of plants relating to vigor, yield, water or salt tolerance, heat stress, or the like, appears initially to be a more difficult objective. The traits which are associated with these qualities are poorly understood, and the gene, or more likely, genes, associated with the various traits are generally uncharacterized. Accordingly, there is a need to identify new classes of traits, or genes, which can be inserted into crop plants to attempt to make them grow better. Even if newly inserted genes do not make a plant perform better in agricultural conditions, transgenic plants carrying such genes are useful for research purposes for investigating how changes in plant internal processes (e.g. osmotic regulation) affect the field performance of the plants.

All plants, of course, capture energy in the form of sunlight and store energy in a chemical form as sugars.

However, the sugars which plants manufacture vary in kind and relative amounts from plant to plant. In addition to serving their function of chemical energy storage, some sugars or other carbohydrates may also serve to regulate the osmotic balance of the plants. The osmotic ability of the plant cells, and the relative osmotic balances among the subcellular organelles, may be fundamentally related to the ability of plants to withstand stresses of a variety of types, such as freezing or salt stress, in addition to drought or water stress. Cold, for example, may be fatal to plant tissues due to water loss long before temperature extremes are reached at which ice would crystallize inside plant tissues. This ability to withstand water stress may be fundamentally related to plant performance in adverse conditions.

The role of polyalcohol sugars, or polyols, in plant metabolism is poorly understood, in spite of the fact that up to 30% of the annual global carbon production by higher plants may go into polyols rather than simple sugars. Of the polyols, mannitol is the most abundant in nature. While it is found in about seventy plant families, it is not produced at detectable levels in any important agricultural field or vegetable crop, other than celery (Apiaceae), coffee (Rubiaceae) and olive (Oleacea). Mannitol is quite commonly produced in algae and fungi.

Other polyols are common in some plant species, even in some instances in which no metabolic role for polyols are apparent. For example, the polyols ononitol and pinitol are known to be produced in some plants under conditions of stress from drought, salt or low temperature. In some of these plants, the polyol produced appears to be a dead-end product, i.e. one which has no further metabolic role and from which no other metabolite is synthesized. This raises the possibility that the accumulation of such polyols serves an osmotic regulatory role.

In plants, there are two separate pathways for mannitol biosynthesis. One pathway used, for example in brown algae, proceeds from the reduction of fructose-6-P to mannitol-1-P by mannitol-1-P dehydrogenase, with an NAD cofactor, followed by dephosphorylation by a specific mannitol-1-P phosphatase. (Mannitol-6-P and mannitol-1-P are synonymous.) In celery, the process is different, beginning with mannose-6-P, which is reduced to mannitol-1-P by mannose-6-P reductase with an NADP cofactor, followed again by dephosphorylation.

In *E. coli*, a mannitol catabolic system is known. In *E. coli*, mannitol is taken in from the environment and converted by phosphorylation to mannitol-1-phosphate (M1P). Then the NAD dependent enzyme, mannitol 1-phosphate dehydrogenase, (M1PD) converts the mannitol-1-phosphate to fructose 6-phosphate in an equilibrium reaction. The gene coding for this enzyme, referred to as mtlD, has been previously cloned by others.

One approach to evaluate the role of polyols in plant stress response is to examine polyol production in stress tolerant plants. There are a number of salt tolerant plants, referred to as halophytes, which are relatively tolerant to drought and cold, as well as salt. Unfortunately, most of our important crop plants are salt-sensitive species, referred to as glycophytes. If the genes and mechanisms used by halophytes to combat stress are identified, it may become possible to transfer those genes and/or mechanisms into important crop plants by genetic engineering.

One unique system that can be used to identify stress tolerance genes and mechanisms is the inducible halophyte, *Mesembryanthemum crystallinum*, the common ice plant. As a facultative halophyte, the ice plant undergoes a set of stress-induced biochemical changes to become more stress tolerant. One of those changes involve a switch of metabolic pathways, i.e. from $C_3$ to crassulacean acid metabolism, as a water conservation measure. Others of those changes were heretofore poorly characterized.

SUMMARY OF THE INVENTION

The present invention is summarized in that transgenic plants are created which have altered production of one or more sugar alcohols, or polyols, the transgenic plants being genetically engineered to produce novel polyols in physiologically significant quantities.

The present invention is also summarized in that a method for altering the carbohydrate constituents of higher plants by genetically transforming into the genome of the plants a gene conditioning the expression of an enzyme which catalyzes the synthesis of a polyol not natively produced by that plant species from endogenous sugars.

It is an object of the present invention to describe a novel approach to the genetic alteration of higher plants so that useful crop plants with new traits can be made and so that research in the improvement of crop plants can be fostered.

It is another object of the present invention to genetically engineer plants which do not natively produce mannitol to produce mannitol. The production of mannitol in such plants is useful for research purposes, and may be agronomically useful due to the enhanced stress tolerance of the engineered plants.

It is yet another object of the present invention to genetically engineer plants which do not natively produce ononitol to produce ononitol. The production of ononitol, or its metabolite pinitol, may also increase stress tolerance in glycophyte plants.

It is yet another object of the present invention to alter plants to produce new carbohydrates in growing plants without deleterious effects to the plant.

It is a surprising feature of the present invention that transgenic plants producing mannitol, which are of a plant species which does not natively produce mannitol and which has been reported to poorly metabolize mannitol, if it can metabolize it at all, are not deleteriously affected by the presence of mannitol in their tissue, but actually appear to have increased in vigor and stress tolerance.

Other objects, features, and advantages of the present invention will be apparent from the following specification when taken in conjunction with the accompanying drawings.

DETAILED DESCRIPTION OF THE INVENTION

Figure 1:
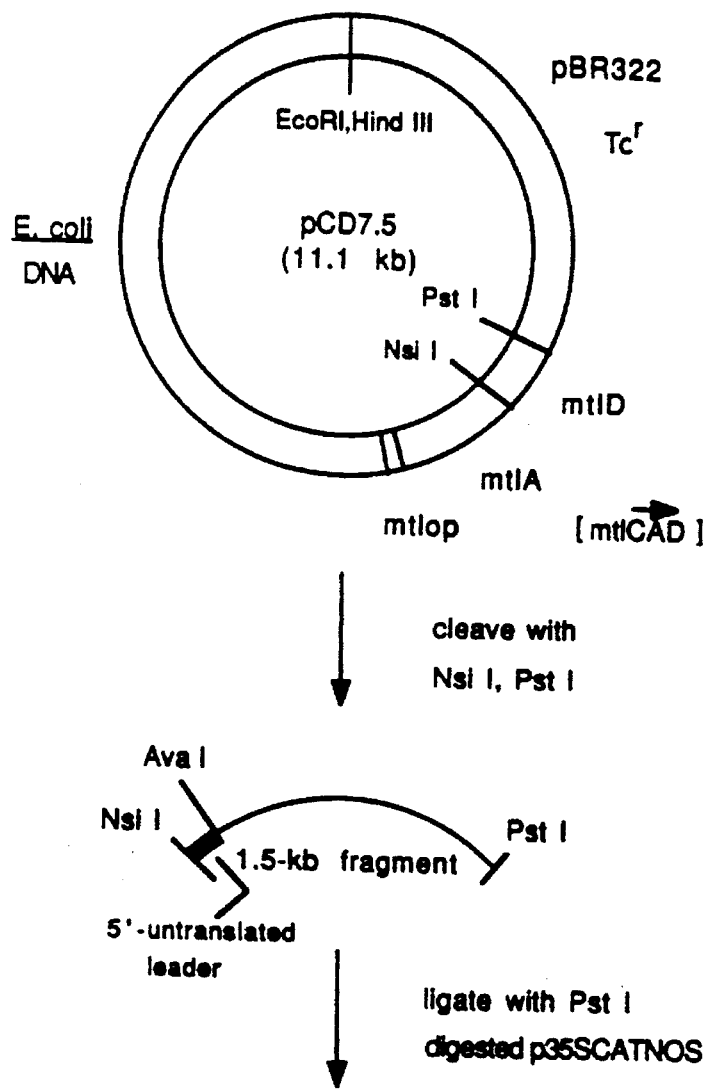
FIG. 1 is a schematic illustration of the construction of the plant expression vectors p35SMTLDL and p35SMTLDS.
Figure 2:
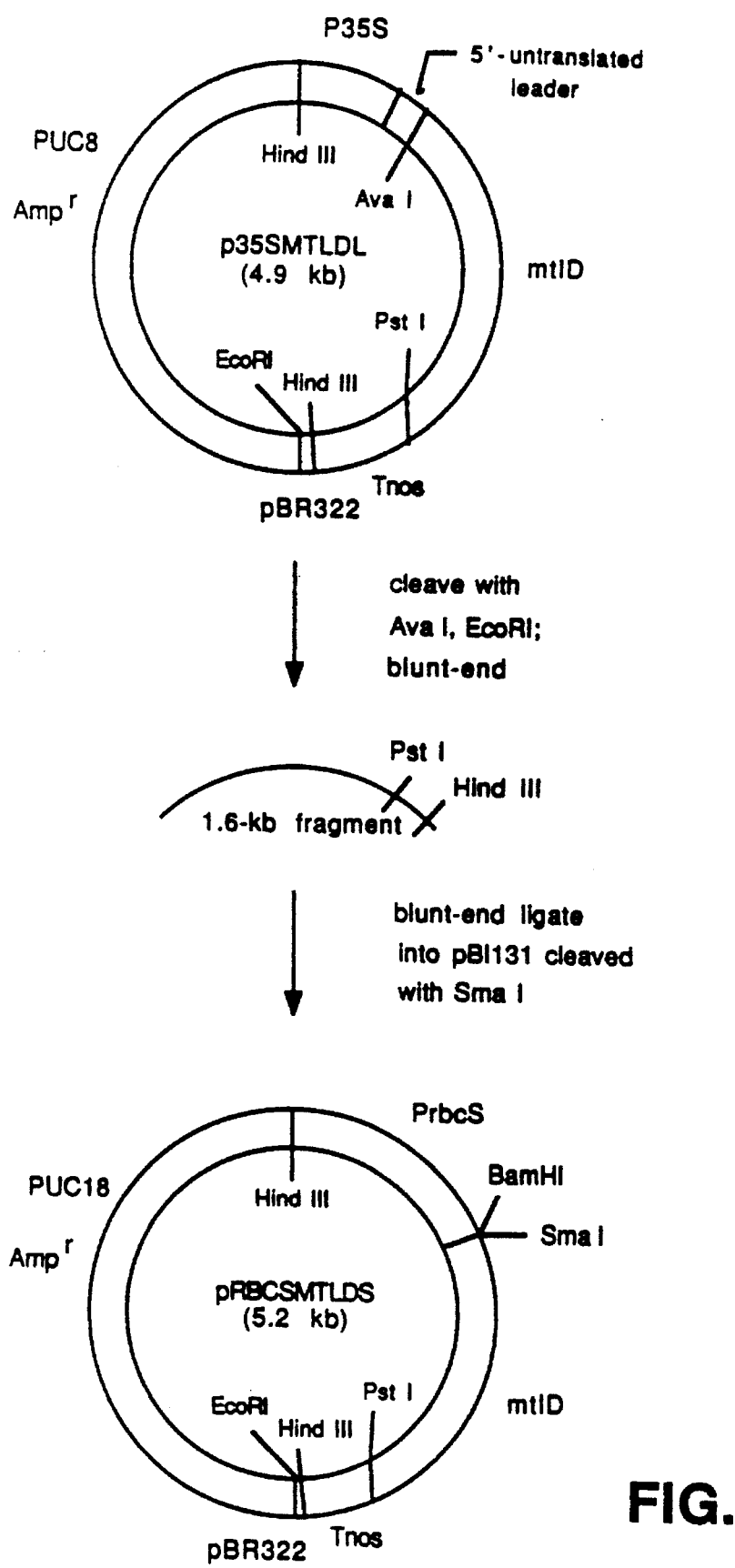
FIG. 2 is a schematic illustration of the construction of the plant expression vector pRBCSMTLDS.

The present invention is directed to a method of genetically engineering of plants so as to produce altered, agronomic or physiological changes in the plants by the alteration of the production of polyhydroxylated sugars, or polyols, within the tissues of the plants. In particular, it has been found that it is possible to genetically engineer a plant which does not natively produce a particular polyol, such as mannitol, to produce physiologically measurable quantities of the polyol as a metabolic product, from precurser sugars normally present within the tissues of the plant. Surprisingly, the production of mannitol by a plant which does not natively produce it not only fails to create any adverse impact on the plant, it seems to foster the growth of the plant resulting in a visibly more vigorous and healthy plant. This result has been achieved by introducing into the genome of a plant a foreign gene coding for expression of a bacterial enzyme, which is capable under physiological conditions present in the cytosol of plant cells, to catalyze the production of mannitol from fructose.

It has also been found that one of the stress-induced mechanisms in facultative halophytes also involves the synthesis of polyols. By identification and cloning of one of the genes responsible for such stress-response, it now becomes possible to begin to directly transfer stress-tolerance traits related to polyol production into glycophyte species.

The work that gave rise to the invention described herein began as an investigation into the feasibility of the alteration of the relative carbohydrate constituents of plant tissues. As the technology for genetic engineering has became more widely known and appreciated, one consequential inquiry has been directed toward what useful changes could be made to plants so that they may be more readily manipulated, ultimately for better agronomic purposes. Alterations in the production of polyols, or sugar alcohols, in plants also has an immediate research utility, in demonstrating the variations and alterations which can be made in plant osmolytes, so that the osmotic balance of plant tissues can be better understood.

One of the objectives of the genetic manipulation of plants is to produce plants which are more resistant to stresses in the field environment. The overall adaptability of plants to water and salt stresses appears to be dependent upon the osmotic adjustments which can be made by plants during times of stress, and the ability of the plants to make such osmotic adjustments appears to be dependent on a number of compatible cytosolutes generated within the cells of higher plants. Higher plants generate a variety of compatible cytosolutes. Included within those compounds are various sugar molecules, including oligosaccharides and polyols. Thus, one possible way to test the ability of plant genetic engineers to vary the stress sensitivity of plants would be to alter the polyol production within a given plant, and to use that plant to investigate what effects could be achieved. It was not clear prior to the results reported here that this objective was possible. In theory, if one introduces into a plant the ability to synthesize a non-native compound from an abundant substrate, in the absence of a metabolic pathway for the compound, one might expect the plant tissues to accumulate excess amounts of the compound, to their detriment. For example, one might expect that polyol biosynthesis would remove plant endogenous metabolics from wild type plants and thus alter wild type metabolic pathways to the detriment of the transgenic plant. Surprisingly, what has been found is that relatively large amounts of a polyol such as mannitol can be produced in plant tissues without harm to the plant, even though that plant species has been reported to poorly metabolize mannitol. In addition, and even more surprisingly, it has been found that the introduction of a single gene which enables the production of a single polyol can have an apparent enhancement of vigor and productivity in a plant (i.e. mannitol accumulation), and can clearly result in significant biochemical alterations of the plant, without undue stress or harm to the plant. In fact, the transgenic plant actually becomes more stress tolerant.

Another route of inquiry into the same problem was directed toward characterizing the stress-response mechanisms of stress-tolerant plants. This inquiry was directed toward the common ice plant, *Mesembryanthemum crystallinum*, because this plant is an inducible halophyte. By study of the mechanisms which are induced in the plant by stress, and contrasting those mechanisms with those of the plant in its non-induced state, a better understanding is achieved of methods for imbuing glycophyte plants with stress tolerance.

It has been found here that one of the stress responses in the ice plant is the transcriptional induction of a gene encoding a novel methyl transferase. This methyl transferase has been identified by functional assay as a myo-inositol O-methyl transferase, and is involved in the ice plant in the biosynthesis of the cyclic polyol D-pinitol. Pinitol is abundantly produced in a number of salt and stress tolerant species, and in the ice plant it can accumulate to over 70% of the soluble carbohydrate of the plant. Paul and Cockburn, *Jour. Exp. Bot.* 40:1093–1098 (1989). Because myo-inositol is an ubiquitous plant metabolite, the availability of the gene encoding myo-inositol O-methyl transferase, referred to here as Imt1, makes possible the introduction of this single gene into a large number of target plant species to cause accumulation of ononitol in those plants, by methylation of myo-inositol.

Thus, as described below, two separate genes are described which are capable of inducing novel polyol biosynthesis in transgenic plants. One gene is bacterial in origin and the other derives from a stress tolerant plant. Thus it is apparent that a variety of techniques for effectuating polyol accumulation in plants for stress tolerance in plants are possible. Each of the two exemplary genes enabling these techniques are described below.

Mannitol Production Gene

The gene of bacterial origin was used to demonstrate that transgenic tobacco plants have been created which can produce mannitol and which have an increased tolerance for salt. Prior to the work described here, it was unknown if plants could be altered to produce mannitol without adverse consequences. In fact, since the plant species investigated, tobacco, does not normally produce mannitol, the production of mannitol in the plant cells could rationally have been expected to be adverse to those cells. Tobacco would not normally be expected to have a degradation pathway for a chemical, i.e., mannitol, which it does not normally produce, and has been reported to poorly metabolize it, Thompson et al., *Physio. Plant.*, 65, pp. 365–369 (1986). Based on this, reasonable expectation of the production of mannitol would be an over abundance of mannitol in the cells of the plant, leading to osmotic imbalance and the eventual bursting or deformation of plant cells. In fact, for reasons that are yet obscure, this has not been the case. In fact, endogenous systems within the tobacco plant appear capable of handling and reacting with mannitol, in particular transporting it systemically within the plant preferentially to certain portions of the plant itself. Thus, and surprisingly, the production of a unique polyol not natively present in a plant species has not only filed to harm the plant, but the plant seems quite capable of managing the existence of the polyol within its tissues and of transporting the polyol preferentially within the plant without additional modifications to the plant genetics being required.

The inventors of the present invention thus began with the goal in mind to alter the polyol production characteristics of higher plants. To do so required the production in plant cells of a heterologous or foreign enzyme which would catalyze the production of a desired polyol within the cells of plant tissues. The enzymes which catalyze the production of polyols in higher plants were, prior to the work described here, generally poorly characterized. Clones for the genes for these plant enzymes were not yet available. Therefore, the search for a suitable enzyme gene to be transformed into plant cells was first directed toward genes for enzymes which have been characterized in bacterial systems. Since enzymes vary in their efficacy over a range of pHs, it is appropriate to search for a gene for an enzyme which would operate in the pH range of plant cytosolic conditions. The enzyme should utilize a substrate which was present in sufficient quantities in both the cytosol of plants and in the chloroplasts. The concentration of the substrate within the cytosol, and the chloroplast, should be sufficient so as to produce sufficient quantities of the polyol to result in biochemical changes to the plant which can be detected by a reasonably convenient assay. It is also preferred that the enzyme either use a readily available co-factor, or no factor, so that catalysis could proceed in a transgenic plant which had a single transforming gene inserted into it. Therefore it is preferred that the enzyme be a simple enzyme, one without additional subunits or co-factors required.

The search for an enzyme meeting the above conditions was conducted, which resulted in the identification of an enzyme known as mannitol-1-P dehydrogenase (M1PD) which was identified in *E. coli*. The gene for this enzyme was cloned and been available to researchers in molecular biology, as described by Lee and Saier, *J. Bact.*, 153:2, pps. 685–692 (1983). The gene for the M1PD enzyme is referred to as mt1D. In *E. coli*, the enzyme is involved in the catabolism of mannitol, which is a carbon source for the bacteria. Mannitol is phosphorylated by the bacteria to make mannitol-1-phosphate, which is then dehydrogenated by the M1PD enzyme to make fructose-6-phosphate. The only co-factor for the reaction is NADH. The reaction is reversible, and the enzyme is a single polypeptide requiring no additional subunits and is thus active as a single unit. The coding sequence for the bacterial gene coding for expression of this enzyme is presented as SEQ ID: NO: 1, below, which contains the coding sequence for mt1D. This bacterial enzyme operates efficiently at an optimum pH between 6.5 and 8.5, which is compatible with plant cytosolic conditions. The substrate for the biosynthesis of mannitol-1-P is fructose-6-P, which is plentiful within the cytosol of all higher plants. In addition, the co-factor, NADH, is also present in higher plants. Accordingly, all the conditions necessary for the synthesis of mannitol-1-P from fructose-6-P by the introduction of a gene encoding this single enzyme seemed in theory to be present in the tissues of tobacco. Until the plants were created, it was not clear that these conditions were sufficient.

In the transgenic plants described here, mannitol is clearly being produced in physiologically significant quantities. The deduced pathway for mannitol synthesis is that fructose-6-P is created from free fructose by a native process in the plant's cells. Fructose-6-P is a natural indirect product of the photosynthetic sugar production process. The fructose-6-P is converted into mannitol-1-P by the M1PD enzyme expressed by the mt1D gene. The mannitol-1-P is then dephosphorylated by a non-specific phosphatase native to the plant. While the conversion of fructose-6-P to mannitol-1-P may be in thermodynamic equilibrium, the dephosphorylation of mannitol-1-P is highly favored and thus this route of synthesis does not suggest how the mannitol may thereafter be metabolized.

The transgenic tobacco plants produced by the insertion of the mt1D gene are not deleteriously affected by the presence of the gene. To the contrary, the transgenic plants seem at least as healthy and vigorous as non-transformed controls. In addition, the transgenic plants have proven to have an increased level of salt tolerance. In controlled experiments, transgenic plants expressing the mt1D gene have remained vigorous under conditions deleterious to control plants. Thus the ability of polyol accumulation to increase stress tolerance is demonstrated.

As described briefly above, several techniques for the introduction of foreign single gene traits into higher plants are now generally widely known, and can be practiced by those of skill in the art. Coding sequences for introduced proteins, such as the mt1D coding sequence in SEQ ID: NO: 1 below, can be combined with suitable flanking regulatory sequences, such as promoters and terminators, to produce expression cassettes which can be transformed into plant cells. A variety of techniques can be used to introduce such plant expression vectors into plant cells. The first developed and most widely used technique is, as described above, based on the infectious mechanism of *Agrobacterium tumefaciens*. However, other techniques such as electroporation of protoplasts, and the accelerated particle delivery of nucleic acids to the interior of plant cells, have also been developed and demonstrated to be effective in creating transgenic plants. It is also known and recognized in the industry that the introduction of a plant expression cassette carrying one or two genes into the genome of a plant results in transgenic plants which are capable of transmitting the inserted transgenes through normal Mendelian inheritance to their progeny. While there is some variation in the various families, or lines, of plants produced using such plant transformation techniques, the variations are stable within plant lines or families, and appear to be dependent upon such variations as copy number and locus of genetic insert into the genome of the plant. As will be described below, the inventors here have created many different independent plant lines incorporating the mt1D gene under various promoters, and all are effective to produce mannitol in the transgenic plants in easily measurable quantities. The inserted gene is fully inheritable by Mendelian inheritance and is effective whether present in a homozygous or heterozygous plant.

What is proposed herein is that the same methodology may be applied to other higher plants which do not natively produce mannitol. None of the major field crops, such as the grains, including corn and wheat, and other field crops such as cotton and soybean, and the major vegetable crops, other than celery, produce mannitol at detectable levels or above approximately 5 milli-Molar. It has been found herein that the introduction of a single gene into tobacco plants results in relatively large levels of mannitol production within the cytosol of the plants. Levels of mannitol in excess of 100 milli-Molar are found to be readily measurable, and effective to cause visible enhancement of the general vigor and growth of the transgenic plant into which the mannitol production trait has been inserted. It is specifically intended, and envisioned herein, that mannitol production can thus be created in other plant species both as a laboratory tool to investigate the catabolism and storage characteristics of polyols in these plant species, and potentially as a strategy to induce increased agronomic or agricultural performance for the transgenic plants thus produced.

As a variant of the present invention, it is also intended that the mt1D gene be inserted into transgenic plants so as to preferentially produce mannitol in the chloroplasts in the transformed plants. The presence of the enzyme, and thus mannitol, is desired to be present in the chloroplasts specifically on the theory that the osmotic protective effects of mannitol will be more pronounced if present in the chloroplasts. This may be done by placing the mt1D coding sequence in a plant expression cassette including a 5' transit peptide sequence which causes transit of the expressed peptide preferentially into the chloroplasts. One such transit peptide expression cassette is described by Guerineau et al., *Nucl. Acids Res.* 16:23, p. 11380 (1989). As it becomes possible to directly transfer genes into cellular organelles, this may also prove useful to control the site of mannitol synthesis.

Imt1 Gene

As stated above, another avenue of inquiry was toward the identification of mechanisms in the salt tolerant halophyte, *M. crystallinum*, the ice plant, to identify genes responsible for its inducible salt tolerance. To investigate the molecular basis of this inducible salt tolerance, a subtracted cDNA library was created which was enriched for stress-induced sequences. The cDNA library was then analyzed to identify those transcriptional products which were preferentially, or dramatically, increased in expression in the plant following stress induction. This was done by comparing the cDNAs from stressed and unstressed plants. A number of cDNAs were identified which were dramatically up-regulated during the process of stress response. Cross hybridization experiments ultimately indicated that three distinct clones were identified from those cDNAs. One of the clones has been identified as a gene encoding an enzyme, myo-inositol O-methyl transferase, here denominated by the name Imt1. The methyl transferase enzyme is involved, in the ice plant, in the biosynthesis of the cyclic polyol pinitol. Pinitol is an abundant metabolite in the salt-stressed ice plant. This transcriptional induction of the biosynthesis of the Imt1 gene in the stressed ice plant indicates that the production of the polyols plays a crucial role during the adaptation to osmotic stress by this facultative halophyte.

In the ice plant, the pathway of production of pinitol begins with glucose-6-P which is converted into myo-inositol-1-p and then into myo-inositol. In general, myo-inositol can be converted by a methyl transferase into either sequoyitol or D-ononitol, depending on the plant species, which are then converted into D-pinitol. In the ice plant, it is D-ononitol that is made. The Imt1 enzyme is believed to perform the methyl transferase function to convert myo-inositol to D-ononitol.

The cDNA clone containing the coding region for the gene Imt1 has been determined. The sequence is presented as SEQ ID: NO: 3 below. The cDNA clone is 1524 base pairs long and includes a leader sequence rich in A and T residues, and an ATG start codon, followed by an uninterrupted open reading frame of 1095 nucleotides. Analysis of the coding sequence for the Imt1 gene predicts a hydrophilic protein of 365 amino acids with a molecular weight of about 40 kD. A search of the NBRF genetic data base reveals a similarity to a bovine pineal gland hydroxyindol O-methyl transferase, which was homologous over 55% of the entire length of the protein coding region. The predicted protein product from the Imt1 gene was found to be even more closely related to two plant bifunctional hydroxymethyl transferases, which methylate the lignin monomers caffeic acid and hydroxyferulic acid, having in excess of 50% identity over the entire length of the protein coding region.

All this suggests that the possible role for this methyl transferase in the salt stress response in the ice plant is the initiation of the biosynthesis of pinitol. Pinitol accumulates to high levels in the ice plant at the same time as the transcript of the Imt gene appears at high levels in the cytosol of the plant. To substantiate the hypothesized physiological role of the Imt gene in pinitol biosynthesis, the gene has been introduced into a suitable expression vector and expressed in *E. coli*. The bacterial lysates from the transformed *E. coli* were tested for myo-isotol hydroxymethyl transferase activity. In that lysate, a protein of molecular mass of approximately 40 kD was identified which co-migrated on polyacrymalide gels with a translational product created by transcribed copies of the Imt1 clone created in vitro. Extracts from *E. coli* cells, both control cells and cells expressing the Imt1 gene, were assayed for myo-inositol-dependent O-methyl transferase activity was conducted. The expected activity in the transformed extracts was found and the activity was lacking in the controls. The enzyme produced by the Imt1 gene was found capable of methylation of myo-inositol to produce ononitol, the methylated intermediate in pinitol biosynthesis.

The fact that an inducible gene associated with stress tolerance in an inducible salt-tolerant plant is responsible for the synthesis of a cyclic polyol is highly supportive of the thesis that accumulation of polyols in plant cells is associated with increased stability to withstand stress. This conclusion is thus supported by data of two independent types. First, as noted in the first example described above, a bacterial gene encoding an enzyme capable of conditioning the production of polyols in plant cells has given the plant enhanced stability to withstand salt stress. Secondly, the native genes found in plants also associated with salt stress do include genes encoding enzymes responsible for polyol synthesis. Hence both observations support the conclusion that otherwise stress intolerant plants can be made more stress tolerant by the introduction into those plants of gene systems encoding enzymes responsible for polyol accumulation in the cells of those plants.

It is also believed that the surprising results achieved here suggest that other non-native polyols may also be produced in crop plants without damage to the plants and with potential benefit. Suitable enzymes can be found to produce in plant cells other sugar alcohols, such as ribitol, erythritol, xylitol, arabitol, sorbitol, inositol, methyl-inositol, dulcitol, galactitol and heptitol. In addition to the sugar alcohols identified above, the term "polyol" as used here is intended to apply to both the polyalcohol sugars plus immediate derivatives of them, such as methylated polyols. These other polyols can be produced in higher plants by a method similar to the production of mannitol described here, i.e. by identifying enzymes which can catalyze the synthesis of the desired polyol from available substrate in the plants' cells and by introducing a gene for the enzyme into transgenic plants. The transgenic plants thus produced will accumulate in their cells one or more polyols not natively produced by plants of that species, or present in plants of that species only in much lower amounts. Producing a polyol in a plant in amounts ten times greater than native levels may produce stress-resistance, and levels of polyols in excess of 20 to 100 times greater than native plants can readily be obtained.

The following are examples reciting the precise protocol used by the inventors here. It is to be understood that these examples are illustrative of the present invention and not limiting thereof.

EXAMPLES

Example 1: Bacterial mt1D gene

Construction of plant expression vector/plasmids

The construction of the plasmid p35SMTLDL began with the plasmid pCD7.5, which is described in Lee and Saier, J. Bact. 153:2, pp. 685–692 (1983). The digestion of copies of pCD7.5 with the restriction enzymes NSI 1 and Pst I resulted in a 1.5 kilobase fragment, which contained the entire *E. coli* coding region for the mt1D structural gene together with 150 base pair untranslated leader sequence. This 1.5 kilobase fragment was then subcloned into the Pst I site of an expression vector derived from p35SCATNOS, from which the CAT gene had been deleted. The plasmid p35SCATNOS has been described by Fromm et al., *Proc. Natl. Acad. Sci. (USA)* 82, pages 5824–5828 (1985) and Fromm et al., *Nature*, 319, pages 791–793 (1986). The subcloning of the fragment into the expression vector resulted in a plasmid designated p35SMTLDL. This procedure is illustrated schematically in FIG. 1.

Figure 3:
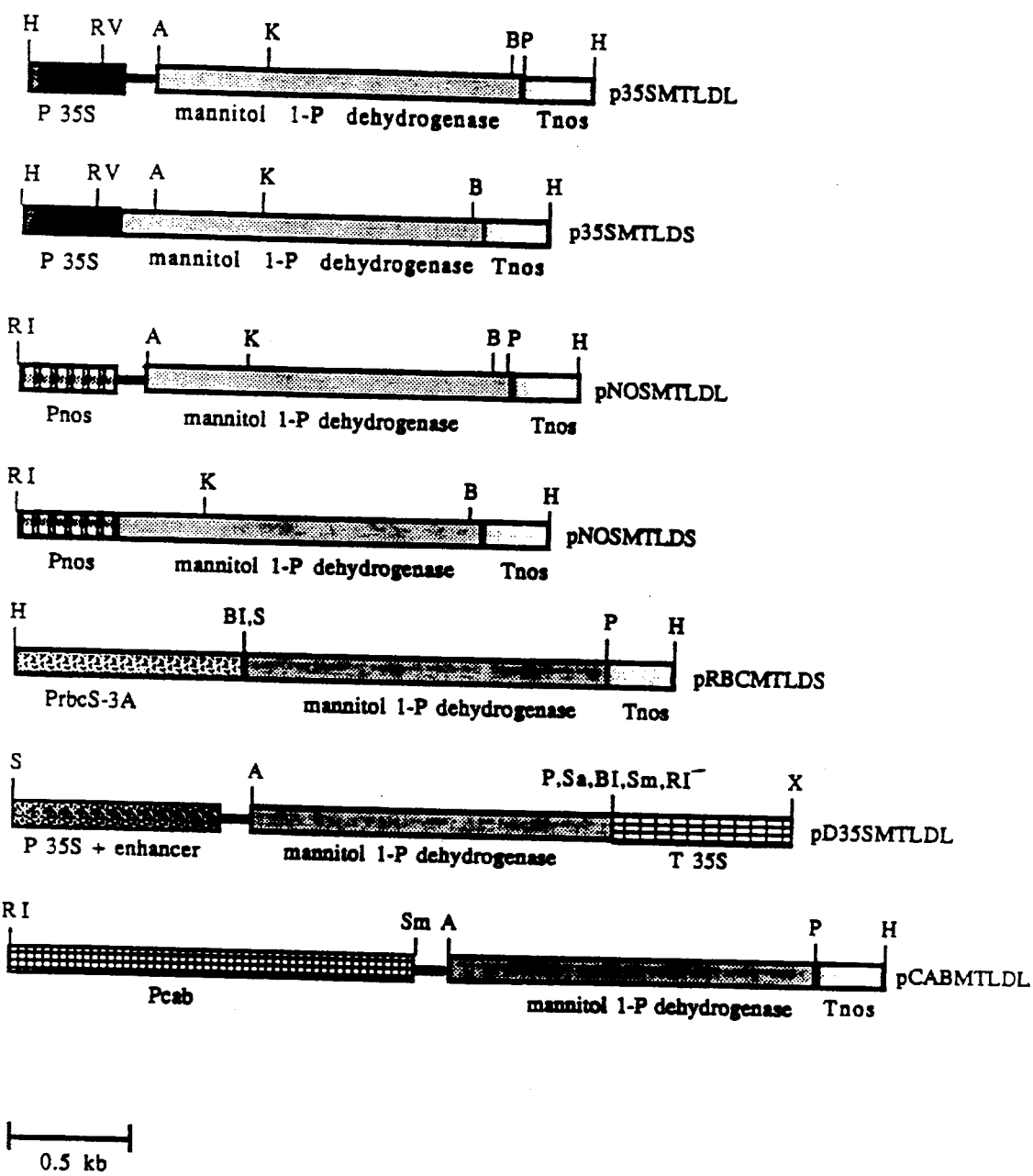
FIG. 3 is a chart illustrating the various expression vectors constructed by the inventors here.

This vector was then altered to delete the 150 base pair 5' untranslated leader from the bacterial mt1D structural gene, by blunt-end subcloning the fragment produced by digestion of p35SMTLDL with the enzymes Ava 1 and Pst I into additional copies of the plasmid p35SCATNOS, creating an alternative expression vector designated p35SMTLDS. The suffixes "L" and "S" represent "long" or "short," referring to the leader sequence. Both of the vectors p35SMTLDL and p35SMTLDS included coding regions for the gene mt1D located behind the cauliflower mosaic virus 35S promoter, a promoter known to be highly active and resulting in a high level of expression of foreign genes transformed into plant cells. The vectors may be compared by reference to FIG. 3.

A second set of expression vectors contain the mt1D gene behind the nopaline synthase promoter from pNOSCAT-NOS, also described by Fromm et al. supra. The manipulations were exactly analogous to those described above, creating two plasmids designated pNOSMTLDL and pNOSMTLDS, each of which included the mt1D structural gene located behind the nopaline synthase promoter from *Agrobacterium tumefaciens*.

Additional copies of the plasmid p35SMTLDL were digested with the enzymes Ava I and Eco RI, and then blunt ended. The resulting 1600 base pair fragment was then isolated by electrophoresis and ligated to a plasmid designated pBI131, as described by Jefferson et al. in *EMBO Journal* 6, pages 3901–3907 (1987), which had been digested with Sma 1, creating a vector designated pRBC-SMTLDS. This vector contained as a promoter the rubisco small subunit promoter from tobacco, which has previously been demonstrated to be a light activated promoter, conditioning expression of genes only in photosynthetic tissues or other tissues of plants exposed to incidental light radiation.

An additional plasmid pD35SMTLDL was created, in a manner similar to p35SMTLDL, except that the expression vector pJIT117, described by Guerineau et al., *Nucleic Acids Research* 16:23, p. 11380, (1988), was digested with the enzymes Hind III and Sph I, blunt-ended, religated, and then digested with Pst I. This plasmid contained the mt1D structural gene located behind a cauliflower mosaic virus 35S promoter, and an untranslated enhancer sequence also from the cauliflower mosaic virus.

The plasmid, pCABMTLDL, was created by separately digesting a plasmid designated pKH111 (Harkins et al., *Proc. Natl. Acad. Sci. (USA)* 87, pages 816–820 (1990)) and the plasmid pUC18 with the enzymes Eco RI and Sma I, isolating the 1750 base pair fragment containing the CAB promoter from the pKH111 digest, and ligating the fragment with the linerized copies of pUC18. The CAB promoter refers to the promoter from the chlorophyll AB binding protein gene. This vector was then digested with Pst I, and the fragment containing the mt1D structural gene above was ligated to Pst I digested pUC18 vector. This vector was then digested with Pst I and ligated to a Pst I digested vector fragment containing the 300 base pair nopaline synthease terminator from p35SMTLDL which was isolated by digestion with Pst I and Eco RI from that plasmid.

All of the plant expression vectors described herein were subcloned into a disarmed binary vector, Bin19, for insertion into plants as described by Bevan *Nucleic Acids Research* 12, pages 8711–8721 (1984). The binary vector system separates the virulence function from the Ti plasmid from the T-DNA. This was accomplished by making Hind III digests of p35SMTLDL, p35SMTLDS, and pRBCSMTLDS and by using Eco RI and Hind III digests of pNOSMTLDL, pNOSMTLDS, and pCABMTLDL. For the plasmid pD35SMTLDL, the digestion was with Sst I and Xho I. Each of these expression cassettes was subcloned into the corresponding restriction sites of the disarmed binary vector Bin19.

Transformation of Plant Tissue

The recipient plant used for all the transformation experiments described herein was tobacco, *Nicotiana tabacum* cv SR1.

To perform the transformation experiments, the Bin19 expression vectors were each separately introduced into cultures of non-oncogenic *Agrobacterium tumefaciens* (strain LBA4404) via the triparental mating technique described by Bevin, *Nucleic Acids Research* 12:8711–8721 (1984). The presence of the gene constructions in the *A. tumefaciens* was confirmed by Southern Blot analysis. The nonocogenic *A. tumefaciens* was then used to perform tobacco transformation/regeneration techniques essentially as described by Horscht et al. *Science* 227 pages 1229–1231 (1985).

Briefly recapitulating the procedure, the *A. tumefacien* cultures were cultured for three days at 28½ C on MSO plates (MSO medium containing one vial per liter of MS salts, 5 ml/l 200×vitamins-20,000 mg/ml myo-inositol, 100 mg/ml nicotinic acid, 100 mg/ml pyridoxine-HCL, 400 mg/ml thiamine-HCL and 400 mg/ml glycine-30 g/L sucrose, pH 5.8 with KOH, 8 g/L agar). The *A. tumefaciens* culture is transferred to 7 milliliters of liquid MSO medium as described above, only lacking agar. After bacterial resuspension, young sterile leaf tissue pieces of the tobacco plants were cut in 0.2 to 0.5 centimeters squares and were incubated for 10 to 20 minutes in the bacterial suspension. The leaf tissues were then transferred onto MSO agar plates, and allowed to co-cultivate with the bacteria for 48 hours at room temperature. Following co-cultivation, the leaf tissue was transferred to a shoot inducing medium designated MSS, which consists of the MSO medium and agar plus 0.5 mg/L 6-benzyl amino purine, 400 mg/L carbenicillin and 400 mg/L kanamycin, on which the shoots were allowed to grow for about four weeks. The resulting tobacco shootlets were cut from the callas tissue and transferred to a root inducing medium, similar to MSS described above except 2 g/l sucrose, 8 g/l glucose and 200 mg/l carbenicillin and 75 mg/l kanamycin. The shootlets were allowed to root for about four weeks. Following rooting, the plantlets were removed from sterile magenta boxes and placed in soil. The plants could then be moved to green house conditions, under which they grew normally into whole sexually fertile and mature tobacco plants. The transgenic plants, as evidenced by mannitol content, were self-pollinated to obtain transgenic progeny and to confirm Mendelian segregation.

Biochemical Characteristics of the Transgenic Plants

The presence and expression of the transgenes in the regenerated (RO) and progeny (R1) plants was confirmed by analysis for the presence of mannitol. No control, nontransformed but regenerated, plants evidence detectable levels of mannitol. Approximately two hundred separate transgenic plant lines containing mannitol have been, recovered. Measured mannitol levels typically exceeded 100 mM in the transgenic plants. Normal levels of the common sugars, sucrose, fructose and glucose, were found to be maintained by the plants that produced mannitol.

To perform the analysis, leaf material segments were extracted from the young axenically grown plants transformed with the constructions p35SMTLDL, p35SMTLDS and pRBCSMTLDS. The leaf material segments, approximately 3 centimeters in length, were extracted for soluble carbohydrate, which was then eluted by high-performance anion-exchange chromatography coupled to amperometric detection (HPAE-PAD), to analyze the carbohydrate content of the tissues, using the technique of Lee, *Analyt, Biochem.*, 189, pp. 151–162 (1990).

Figure 4:
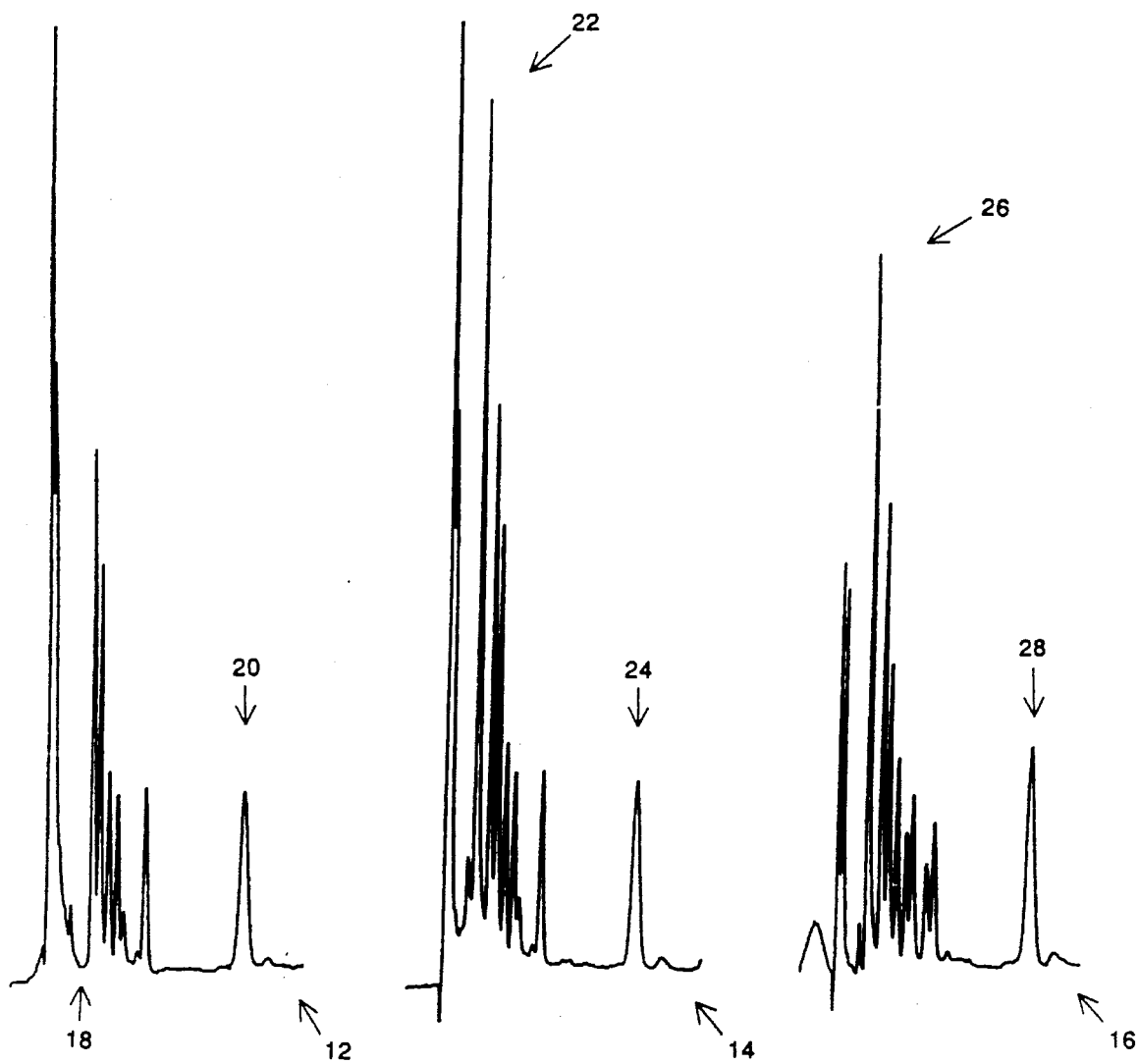
FIG. 4 illustrates three graphical illustrations of the output of high performance anion-exchange chromatography with pulsed amperometric detection (HPAE-PAD) analysis of the soluble sugars of plant tissues.

Results of the HPAE-PAD separation of soluble carbohydrate extracts in the plants is illustrated by three chromatographic separations illustrated in FIG. 4. Within FIG. 4, there are three output representations of the HPAE-PAD analysis of leaf materials. The three chromatographic outputs are designated 12, 14 and 16. Curve 12 illustrates the HPAE-PAD separation output of soluble carbohydrate extract from a leaf of a non-transformed, regenerated control plant. Within curve 12, the reference numeral 18 is placed where the elution characteristic of mannitol would be indicated, and the reference numeral 20 indicates that associated with the simple sugar sucrose.

The HPAE-PAD separation output indicated at 14 represents the chromatographic profile from an extract from a leaf from an untransformed, regenerated plant, to which had been added mannitol in an amount of 0.25 nanomoles, as a positive control. Indicated at 22 is the peak associated with the retention time of mannitol, and indicated at 24 is the peak for sucrose.

Illustrated in curve 16 is the HPAE-PAD separation chromatograph for a transgenic plant transformed with the plant expression vector, p35SMTLDL. Indicated at 26, is the peak associated with the elution characteristic of mannitol, and at 28 is the peak for sucrose.

It can readily be seen with reference to the curves illustrated in FIG. 4 that the transgenic plant exhibits a peak for mannitol production not present in the nontransformed samples. Thus, the transgenic character of the plant is clearly indicated by the presence in the plants of a catalytic reaction product, not present in native transformed tobacco tissues. Similar profiles were found with other transgenic plant families. Mannitol content was often within the range of sucrose content, and on occasion exceeded it.

One surprising and consistent anecdotal observation made during the regeneration of the transgenic plants, transformed with the vectors and genes described herein, is that the transformed plants appeared generally greener and more vigorous than similar nontransformed, control plants being simultaneously regenerated. While it might have been suspected that the production of mannitol would detract from the production of other carbohydrates necessary to plant growth and vigor, it has been found surprisingly that the transgenic plants seem actually to generally outgrow and develop faster and more vigorously than similar plants regenerating from tissue culture which have not been transformed. The exact reason for this apparent increase in growth rate and vigor is obscure, but it clearly indicates that the production of indigenous mannitol within the cells of the plants is not deleterious to overall plant growth and health and may, in a manner yet to be determined, actually be beneficial to the overall health and vigor of the transgenic plants creating this compound within their cells.

Figure 5:
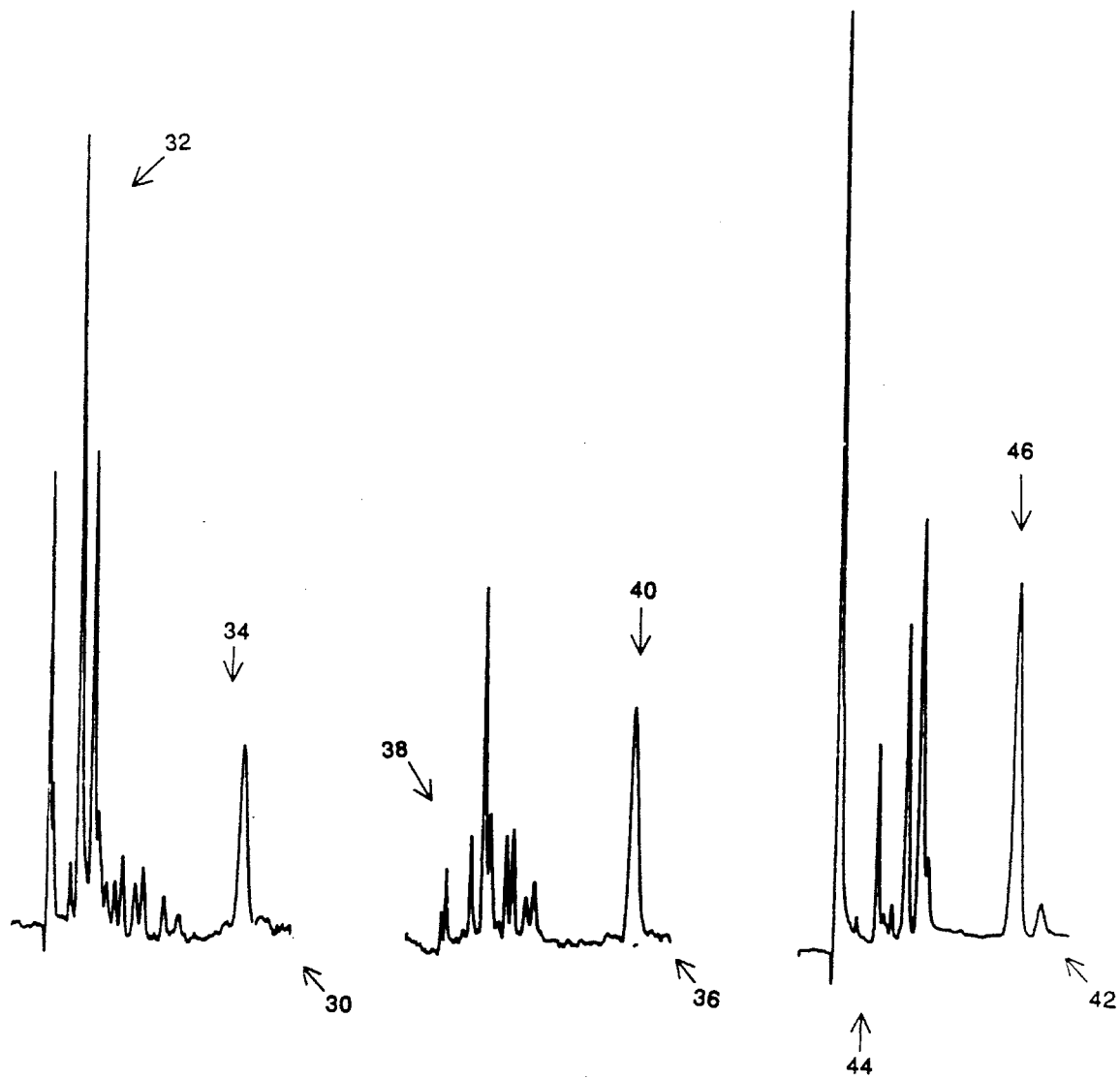
FIG. 5 illustrates another three graphical illustrations of HPAE-PAD analysis of transgenic plant tissues.

Another surprising result produced by the transgenic plants within the present invention is illustrated by the HPAE-PAD outputs illustrated in FIG. 5. These outputs are associated with a transgenic plant which was transformed with the vector pRBCSMTLDS. As it may be recalled, the promoter associated with this expression vector is from the rubisco small subunit, and has been previously demonstrated to be light activated. Therefore, it would be expected that analysis of the various tissue parts of the transgenic plant which contains this particular expression vector would indicate mannitol production only in the leaves or other green tissues of the plant. One might expect to find only trace amounts of mannitol in the subsoil portions of the plant. In fact, surprisingly, this is not the case. Referring to the HPAE-PAD separation chromatographs illustrated in FIG. 5, the reference numeral 30 indicates the characteristic of a HPAE-PAD separation analysis of soluble sugars from the root material of a transgenic plant transformed with this expression vector. In that signal, the position of the peak for mannitol is indicated at 32, and the peak for sucrose is indicated at 34. A second HPAE-PAD output signal is indicated by the reference numeral 36, in which the output position for mannitol is indicated at 38, and for sucrose is indicated at 40. Finally, at 42 a chromatograph is illustrated in which the mannitol location is indicated at 44, and the sucrose position is indicated at 46.

The graph 42 represents, in FIG. 5, the control experiment. The signal is taken from root material from an untransformed, but regenerated plant. As would be expected in this negative control, there is no indication of the presence of detectable mannitol within this root tissue. The signal 36 represents the output from leaf material isolated from a transgenic plant, the same plant from which the root extract in signal 30 was taken. As may be seem from this function, mannitol is present in significant levels within the transgenic plant tissues. Based on the area underneath the curve as illustrated in this figure, mannitol was estimated to be about 8% of the total sugar content of the leaf material, and was clearly several times less than that of sucrose. What is surprising is that graph 30 represents the separation of soluble sugars from root material from that same plant. In this curve, it would appear that mannitol represents more than 35% of the total amount of sugars detectable in root material, and appears to be at least several times greater than the abundance of sucrose within this tissue.

This result is unexpected and very surprising. Since mannitol is not natively present within the tissue of tobacco plants, one would not expect that there would be a transport mechanism existing within the plant capable of efficiently transporting mannitol from the leaves to the roots. But apparently, such a system exists, since the promoter giving rise to the mannitol in the plant through soluble sugars are separated in the chromatographs of FIG. 5 was transformed with a light-activated promoter. Accordingly, this would indicate that mannitol is being produced within the leaves, and is being transported through a yet uncharacterized mechanism from the leaves down through the plant for storage in the roots. Clearly the presence of such significant levels of an osmotic protectant in the root offers the potential for stress relief for the plant, by making the plant less sensitive to variations in moisture levels within the soil. Although this result cannot be assured from the research conducted to date, clearly, this establishes that unique and surprising effects of soluble sugar contents of plant tissues are created through the use of this technology, which have results which are surprising and clearly useful in research to ascertain in greater detail the mechanisms of plant sugar storage and transport.

Plant tissues may in the future also be transformed with plant expression vectors constructed to include a transit peptide for chloroplast transport. It is expected that the transgenic plants recovered expressing such vector will preferentially accumulate mannitol in the chloroplasts. Field testing will reveal the extent to which such accumulation confers additional resistance to moisture stress under field conditions.

Salt Tolerance Test of Transgenic Plants

To test whether or not the effects of the introduction of the Mtl1D gene into the transgenic plants truly resulted in tolerance to stress conditions, a controlled test was undertaken comparing the stress tolerance to salt of both the transgenic tobacco plants and control, i.e., untransformed tobacco plants. This test was conducted using salt tolerance, with salt concentration at half sea water-strength.

The growth of both control (untransformed) and transgenic tobacco plants expressing the Mtl1 gene were evaluated for salt tolerance. Both control plants and transformants were grown hydroponically in the same growth room. After four weeks of hydroponics, without exposure to salt, groups of both control and transgenic plants received nutrient solutions which were supplemented with NaCl at 250 mM. The other remaining plants received nutrient solution alone. All the plants were photographed at 3 to 4 day intervals for up to a month. After a month of culture under these conditions, the plants were evaluated for height, fresh weight, and for mannitol content in the root and leaves. Growth perimeters from a total of 3 independent transformants were compared with the controls. Each experimental group (a total of 3) contained at least 4 replicates each of the controls on the transformants.

In the absence of NaCl, both the control and transgenic plants showed no significant differences in height, onset of flowering, or fresh weight as a percentage of initial weight at the commencement of the experiment. However, for each experimental group exposed to salt in the nutrient solution, the mannitol-producing transgenic plants had significantly greater mass at the end of the experiment. The typical transgenic plants appeared visibly more robust and less chlorotic than did the control plants. In several cases, the mannitol-synthesizing transgenic plants not only survived the salt treatment, but the plants continued to grow and ultimately flowered. In virtually all cases, the control plants exposed to salt treatment were unable to survive. Because the transgenic plants containing the mannitol production trait grew in the salt solution, their heights were significantly greater than those of the controls. A side-by-side comparison of plants with and without salt indicated that both control and transgenic plants not exposed to a salt nutrient solution grew taller, flowered earlier, and had greater overall size than plants which were exposed to the salt solution. However, a similar comparison of plants exposed to the salt solution between the control and the transgenic plants revealed that the transgenic plants grew significantly taller, flowered, and had greater overall size than the control plants exposed to salt solution.

Enablement of other Constructs

Presented below is the complete nucleotide sequence for the mt1D gene and the amino acid sequence of the expressed protein. Plant genetic engineers of ordinary skill in the art will be able to utilize this sequence to make expressing mt1D genes either by using hybridization probing to recover the gene from *E. coli*, or to construct synthetic coding sequences using oligonucleotides. However it is done, once the coding sequence has been obtained, it is possible to construct suitable plant expression vectors such as those described above for transformation into plants. It is envisioned that such plant expression vectors can be constructed for use with a variety of crop plants, other than the model species tobacco described herein, so that mannitol can be created in plant tissues which do not natively produce this polyol.

Set forth below are the nucleotide and amino acid sequences for the mt1D gene and corresponding M1PD enzyme. While these sequences are believed completely accurate, given the state of the art in sequence analysis and processing occasional base pair errors may be present. Such errors will not prevent the utilization of this sequence, without undue experimentation, by those of ordinary skill in the art.

Example 2: Plant Imt1 gene

Identification of the Gene

This work was undertaken to identify the environmentally-induced changes in the expression characteristics involved in the adaptation of the ice plant to salt stress. This was done by constructing and differentially screening a subtracted cDNA library enriched for stress-induced sequences. First, cDNA was generated from poly A+RNA that had been isolated from 7-week old soil-grown plants, which had been stressed with 500 mM NaCl for 10 hours. At 10 hours of exposure to salt, normally ice plants start to recover from stress-induced transient wilting, and are beginning to accumulate the mRNAs associated with alterations of the essential metabolic characteristics of the plant. Three cycles of differential screening of approximately $10^5$ plaques with labeled first-strand cDNAs from stressed and unstressed plants yielded 8 inserts which were consistently more abundant in the stressed plant tissues. Cross-hybridization experiments indicated that the inserts represented 3 distinct clones. One of the clones, a 1.6 k.b. insert now referred to as Imt1, was chosen for further analysis.

Expression of Imt1 mRNA

Expression of the Imt1 transcript was analyzed on northern blots of RNA produced from root and leaf tissues of hydroponically grown ice plants. Total RNA was isolated from unstressed plants and also from plants harvested at several time points over the course of a 6-day stress regimen with 400 mM NaCl. The Imt1 cDNA probe hybridized to a salinity-induced mRNA of approximately 1.6 kD in both leaf and root RNA. The pattern of induction differed between leaf and root tissues. In unstressed leaf tissue, the Imt1 transcript product was present at very low levels. The transcript accumulated gradually in stressed leaves, being detectable after 6 hours of stress but inconspicuous until the second day, after approximately 30 hours of stress. Accumulation of the transcript in leaves reached a maximum by the sixth day of salt stress treatment. By contrast, the Imt1 transcript was transiently up-regulated in root tissues, rising from undetectable levels to a maximum level of expression during the second day of stress. Interestingly, the mRNA completely disappeared from roots by the time of maximum expression in leaves. Blot dilutions of both leaf and root RNA indicated that, at times of relative maximum expression, the transcript was 25 times more abundant in leaves than in root.

Genomic Analysis

The Imt1 transcript induced in leaves and roots is encoded by a single nuclear gene or, possibly, a small interrelated gene family. Nuclear genomic DNA from ice plant was digested with various restriction enzymes and resolved by 1% agarose gel and Southern-blotted along with genome copy number equivalent of the cloned cDNA from SEQ ID: NO: 3 below. The blots were probed with $^{32}$P-labeled cDNA fragments and signal intensities were quantified by a Beta scanner (Betagen, Inc.). The probes were specific to either the 5'-coding region or the 3' non-coding end of the cDNA. Probes hybridized with single bands of equal intensity in each lane. High stringency wash conditions were identical to those used for Northern blots. Comparison of the band intensities with their copy number reconstituents suggests that the bands likely represented a single gene.

Sequence Analysis

To gain sight into the biochemical and physiological function of the Imt1 protein, the sequence of the cDNA was determined. That sequence is presented as SEQ ID: NO: 3 below. The sequence is 1524 base pairs long. The sequence contains a leader rich in A and T residues, and an ATG start codon, followed by an uninterrupted reading frame of 1095 nucleotides. The 3' end of the long non-coding region of 383 nucleotides includes two possible adenylation recognition sequences upstream of the 31-base pair polyA tail.

Shown in SEQ ID: NO: 4 below is the predicted protein sequence derived from Imt1 nuclear sequence data. This predicted polypeptide of 365 amino acids would be hydrophylic, with a molecular mass of 40 kD.

Expression of Imt1 and E. coli

To verify the enzymatic activity of the protein encoded by the Imt1 gene, the coding region from the Imt1 gene of SEQ ID: NO: 3 below was incorporated into an expression vector for expression in the bacterial host E. coli. The full Imt1 open reading frame was cloned into a Bluescript KS+ vector as a transcriptional fusion in both orientations behind the T7 polymerase promoters. Constructs were transformed into E. coli strain BL21 (DE3) cells, which contained the gene encoding the T7 polymerase under the control of an isopropyl-beta-thiogalactoside (IPTG)-inducible promoter. A fortuitously located AAGAG sequence in the 5' leader of the cDNA was predicted to act as a ribosome binding site in E. coli. IPTG was added to cultures at a final concentration of 0.5 mM, 4 hours before harvest. The protein expression was analyzed by SDS-polyacrylimide gel electrophoresis on 10% acrylimide gels. Samples were prepared by boiling aliquots of the transformed E. coli cultures for 2 minutes in an equal volume of SDS extraction buffer.

Soluble protein from E. coli transformed with the Imt1 expression construct or native Bluescript KS+ vectors was extracted from 20–200 ml cultures centrifuged at 2500 g for 10 minutes, and resuspended in methyl transferase extraction buffer (MTEB), using 1 ml of MTEB buffer per 20 ml of E. coli culture. The MTEB buffer includes 100 mM Tris-Cl pH 8, 10 mM EDTA, and beta-mercaptoethanol, at 1 ml per 20 ml of culture. The cells were lysed by sonication, and extracts were clarified by centrifugation at 10000 g for 20 minutes. The total protein concentration was determined. Supernatants were either used immediately for assays or stored at −70° C. with 5% glycerol.

With the soluble protein so extracted, methyl transferase assays were conducted. Aliquots of 200 microliter volume containing 1 mg total soluble protein were dissolved in 50 mM Tris-Cl pH 8, 10 mM $MgCl_2$, and 1.0 mM myo-inositol. Assays were pre-incubated at 30° C. for 5 minutes, and initiated by the addition of S-adenosyl-1-methionine (SAM) to a final concentration of 0.5 mM. SAM stock solution contained unlabelled SAM (Sigma) and $^{14}$C-labeled SAM (ICN Biochemicals) at a 50:1 ratio. Assays were carried out at 30° C. for 30–120 minutes and terminated by transfer to ice and chloroform extraction. The aqueous phase was subjected to further processing in HPLC analysis.

For HPLC analysis, samples were prepared by extraction with a 2 times volume methanol/chloroform/water (12:5:3) followed by the addition of 0.4 ml water. A desalting column of HG50WX4 (BioRad) in Amberlite IRA-68 (Sigma) in OH-form was used to desalt extracts and to remove charged species. Samples were dried, dissolved in deionized water, and filtered through a nylon Acrodisc 13 (Gelman). Equal amounts of dissolved carbohydrates from each assay were resolved in a 300×7.8 mM HPX 87 C calcium-form ligand exchange column (BioRad) at 85° C. with a 0.6 ml per minute flow rate using de-gased, de-ionized water as an eluent. Post-column NaOH was added at 0.3M, 0.6 ml per minute, and traces were obtained using a pulse amperometric detector at 35° C. and a Spectrophysic SP4290 intigrator. Fractions were collected at 7.5 seconds or 0.5 minute intervals and scintillation counted.

The result of the HPLC analysis indicated that the Imt1 gene encodes an SAM-dependent myo-inositol O-methyl transferase. The radio active-carbon labeled product of the assays of the E. coli extracts was visible on HPLC traces as a distinct peak with a retention time of slightly under 11.1 minutes. That same peak was not present on assays from control extracts. To establish that the methylated myo-inositol generated by the Imt1 protein was ononitol, the methylated intermediate in pinitol biosynthesis, its retention time was compared to the retention time of methyl-myo-inositol standards. There are 4 mono-methyl-myo-inositol isomers: sequoyitol, ononitol, and D-L-bornesitol. Only ononitol and sequoyitol are possible precursors for pinitol, and only ononitol has been documented as the precursor to pinitol in angiosperms. Extracts from control *E. coli* were spiked with such standards and analyzed in parallel by HPLC. The retention times of sequoyitol and bornesitol were 11.5 and 12.2 minutes respectively. Ononitol, however, displayed a retention time identical to that of the reaction product from the transformed *E. coli*.

These results demonstrate that the Imt1 gene isolated and the sequence of which is presented below, is responsible for an induced production of polyol accumulation as a part of the stress response of the ice plant. Since the full coding sequence of the protein coding region of this gene is presented below, the incorporation of this gene into cloning vectors and the insertion into transgenic plants is now possible. Since the substrate upon which the enzyme acts, myo-inositol, is ubiquitous in plant tissues, another mechanism has been presented here which is capable of transfer into other plant species to induce accumulation of non-native polyols in those plant species.

It is also to be understood that the present invention is not to be limited to the particular embodiments described herein, but embraces all such modifications and variations thereof as come within the scope of the following claims.

We claim:

1. A transgenic plant with enhanced stress tolerance comprising in its cells as an inheritable genetic trait a foreign gene encoding an enzyme catalyzing the production of a polyol in the tissues of the plant from sugars natively present in the plant the polyol not natively produced in the tissues of plants of the species, wherein the polyol accumulates in the cells of the plant without adverse impact on the plant, and wherein the polyol accumulates in the plant at sufficient levels to confer upon the plant an increased tolerance to salt stress.

2. A transgenic plant as claimed in claim 1 wherein the enzyme is bacterial in origin.

3. A transgenic plant as claimed in claim 1 wherein the enzyme is from another plant species.

4. Seed of the plant of claim 1.

5. A transgenic plant comprising in its cells as an inheritable genetic trait a foreign gene encoding an enzyme catalyzing the production of mannitol in the tissues of the plant from a carbohydrate natively present in the plant, the mannitol accumulating at sufficient levels in the cells of the plant to confer an increased level of salt tolerance to the plant.

6. A transgenic plant as claimed in claim 5 wherein the enzyme catalyzes the production of mannitol-1-P from fructose-1-P.

7. A transgenic plant as claimed in claim 5 wherein the enzyme is a mannitol-1-P dehydrogenase.

8. A transgenic plant as claimed in claim 5 wherein the enzyme is encoded by the E. coli mt1D gene.

9. A transgenic plant as claimed in claim 5 wherein the foreign gene is hosted in the nuclear genome of the plant.

10. A transgenic plant comprising in its genome a foreign genetic construct including a protein coding region and flanking regulatory sequences effective to express a protein coded by the coding region in the cells of the plant, the protein being a mannitol-1-dehydrogenase enzyme from E. coli.

11. A transgenic plant as claimed in claim 10 wherein the coding region produces a protein homologous to that produced by the protein coding region of SEQ ID:1.

12. A transgenic plant comprising in its genome a foreign gene expressing a sufficient amount of an enzyme capable of catalyzing the production in the cells of the plant of a sufficient amount of a sugar alcohol not natively produced in a plant of that species so as to imbue the transgenic plant with an increased tolerance to salt stress.

13. Seeds of the plant of claim 12.

14. A method for altering the sugar alcohol constituents of a crop plant of a plant species to increase the stress tolerance of the plant comprising introducing into the genome of the plant by genetic engineering a gene expressing an enzyme which catalyzes the production in cells of the plant of a sugar alcohol not natively produced in plants of the plant species from a sugar which is natively produced in the plants of a plant species, the sugar alcohol accumulating in the cells of the plant at sufficient levels in the cells of the plant to enhance the salt tolerance of the plant.

15. A method as claimed in claim 14 wherein the enzyme is from a bacteria.

16. A method as claimed in claim 14 wherein the polyol is mannitol.

17. A method as claimed in claim 16 wherein the enzyme reversibly catalyzes the dehydrogenation of the mannitol.

18. A method as claimed in claim 14 wherein the genetic engineering is performed using an Agrobacterium-transformation procedure.

19. A method as claimed in claim 14 wherein the enzyme is from a plant.

20. A transgenic tobacco plant comprising in its genome a foreign genetic construct including a protein coding region and flanking regulatory sequences effective to express a protein coded by the coding region in the cells of the tobacco plant, the protein being mannitol-1-dehydrogenase enzyme from *E. coli*, the flanking regulatory sequences including the cauliflower mosaic virus 35S promoter, and the protein catalyzing the production and accumulation of mannitol in the plant.

21. A transgenic tobacco plant comprising in its genome a foreign genetic construct including a protein coding region and flanking regulatory sequences effective to express a protein coded by the coding region in the cells of the tobacco plant, the protein being myo-inositol O-methyl transferase enzyme from *M. crystallinum*, the flanking regulatory sequences including the cauliflower mosaic virus 35S promoter, and the protein catalyzing the production and accumulation of ononitol in the plant.

22. A transgenic plant comprising in its cells as an inheritable genetic trait a foreign gene encoding an enzyme catalyzing the production of mannitol in the tissues of the plant from a carbohydrate natively present in the plant, wherein the enzyme is encoded by the *E. coli* mt1D gene.

23. A method for altering the sugar alcohol constituents of a crop plant of a plant species comprising introducing into the genome of the plant by genetic engineering a gene expressing an enzyme which catalyzes the production in cells of the plant of mannitol from a sugar which is natively produced in the plants of the plant species, the enzyme being mannitol-1-dehydrogenase from *E. coli*.

* * * * *